(12) United States Patent
Ma et al.

(10) Patent No.: US 11,738,209 B2
(45) Date of Patent: Aug. 29, 2023

(54) SYSTEM AND METHOD FOR CORRECTING POSITION ERRORS OF A MULTI-LEAF COLLIMATOR

(71) Applicant: SHANGHAI UNITED IMAGING HEALTHCARE CO., LTD., Shanghai (CN)

(72) Inventors: Boqi Ma, Shanghai (CN); Zihan Li, Shanghai (CN); Yujie Chen, Shanghai (CN); Lang Yu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 17/380,003

(22) Filed: Jul. 19, 2021

(65) Prior Publication Data

US 2021/0346722 A1 Nov. 11, 2021

Related U.S. Application Data

(63) Continuation of application No. 16/547,488, filed on Aug. 21, 2019, now Pat. No. 11,065,472.

(30) Foreign Application Priority Data

Aug. 22, 2018 (CN) .......................... 201810960823.7

(51) Int. Cl.
*A61N 5/10* (2006.01)
*G21K 1/04* (2006.01)

(52) U.S. Cl.
CPC .......... *A61N 5/1048* (2013.01); *A61N 5/1045* (2013.01); *A61N 5/1081* (2013.01); *G21K 1/046* (2013.01)

(58) Field of Classification Search
None
See application file for complete search history.

(56) References Cited

U.S. PATENT DOCUMENTS 10,518,110 B1 * 12/2019 Jimenez-Carvajal .......................
A61N 5/1048
2004/0240621 A1 12/2004 Noguchi
(Continued)

FOREIGN PATENT DOCUMENTS

| CN | 104147712 A | 11/2014 |
| CN | 104667427 A | 6/2015 |
| CN | 106512221 A | 3/2017 |

OTHER PUBLICATIONS

First Office Action in Chinese Application No. 201810960823.7 dated Jan. 16, 2020, 20 pages.
(Continued)

*Primary Examiner* — Hoon K Song
(74) *Attorney, Agent, or Firm* — Metis IP LLC

(57) ABSTRACT

Methods and systems for correcting position errors for a multi-leaf collimator (MLC) are provided. A method may include determining a first position for each of the plurality of leaves. The information associated with the first position may include a first movement direction and a first angle. A movement of the each of the plurality of leaves along the first movement direction may be configured to move toward or away from a center of the radiation field. The method may also include determining an offset value associated with the first position based on the first angle and the first movement direction; and determining a target position of the each of the plurality of leaves based on the offset value.

20 Claims, 20 Drawing Sheets

(56) References Cited

U.S. PATENT DOCUMENTS

2012/0215049 A1    8/2012  Otani et al.
2014/0239204 A1*   8/2014  Orton .................. A61N 5/1045
                                                        250/505.1
2017/0040077 A1    2/2017  Lee et al.

OTHER PUBLICATIONS

The Second Office Action in Chinese Application No. 201810960823.7 dated Aug. 25, 2020, 18 pages.
Lu, Xiaoguang et al., Study of Dose Variations Induced by MLC Weight Effect for IMRT Delivery, Chinese Medical Equipment Journal, 38(3): 90-93, 2017.
Todd Pwalicki et al., Hendee's Radiation Therapy Physics, Fourth Edition, 2018, 3 pages.

* cited by examiner

300

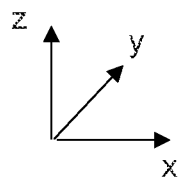
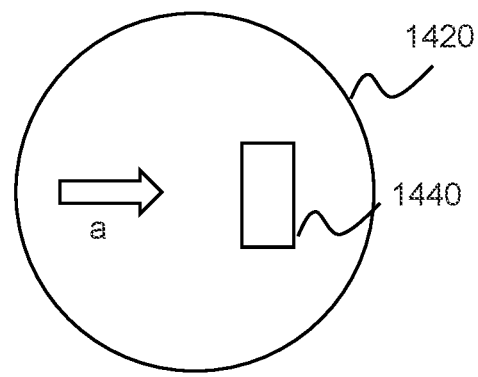
FIG. 14A
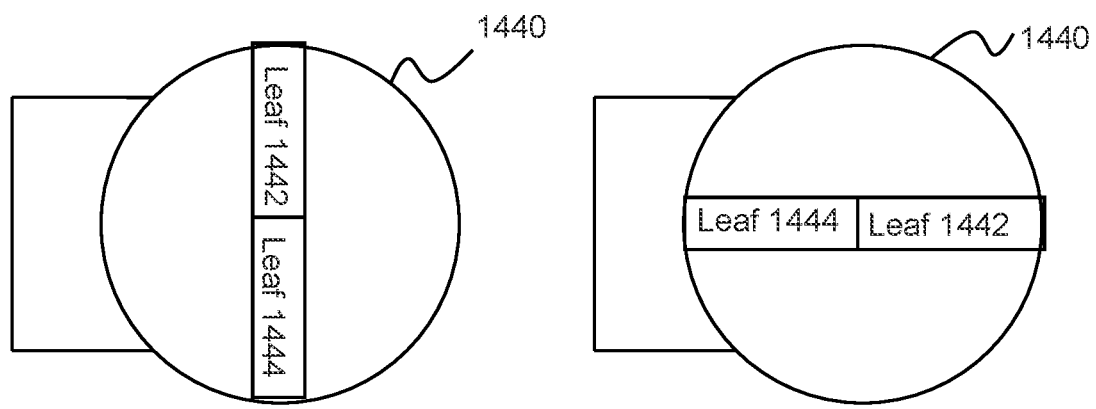
FIG. 14B  FIG. 14C

SYSTEM AND METHOD FOR CORRECTING POSITION ERRORS OF A MULTI-LEAF COLLIMATOR

CROSS-REFERENCE TO RELATED APPLICATIONS

This application is a continuation of U.S. application Ser. No. 16/547,488, filed on Aug. 21, 2019, which claims priority of Chinese Patent Application No. 201810960823.7 filed on Aug. 22, 2018, the entire contents of each of which are hereby incorporated by reference.

TECHNICAL FIELD

The present disclosure generally relates to a medical treatment system and more specifically relates to methods and systems for correcting position errors of one or more leaves of a multi-leaf collimator (MLC) in a radiotherapy procedure.

BACKGROUND

A multi-leaf collimator (MLC) is widely used for collimating radiation beams emitted from a radiation source in radiotherapy systems. The radiation beams collimated by an MLC may be projected to the tumor and an area formed by the projected radiation beams may comply with the shape of a tumor to prevent healthy tissues around the tumor from being radiated. Therefore, the positioning accuracy of the leaves in the MLC is important for precise radiotherapy. At present, the leaves of an MLC are generally driven by motors to move forward or backward to scale a radiation field. In this way, position errors may occur in the movement of the leaves and influence the positioning accuracy of the leaves in the MLC. It is desirable to provide systems and methods for determining an offset value of each of the leaves in an MLC for correcting the position errors.

SUMMARY

According to an aspect of the present disclosure, a method for correcting position error of a leaf is provided. The method may be implemented on at least one machine each of which has at least one processor and storage. The method may include determining a first position for each of the plurality of leaves, information associated with the first position including a first movement direction and a first angle, wherein a movement of the each of the plurality of leaves along the first movement direction is configured to move toward or away from a center of the radiation field; determining an offset value associated with the first position based on the first angle and the first movement direction; and determining a target position of the each of the plurality of leaves based on the offset value.

In some embodiments, the determining a first position for each of the plurality of leaves may include obtaining an angle of a gantry corresponding to the first position of the each of the plurality of leaves; obtaining an angle of a collimator corresponding to the first position of the each of the plurality of leaves, wherein the MLC is mounted in the collimator and rotates along with the collimator; and determining the first angle of the each of the plurality of leaves based on the angle of the gantry and the angle of the collimator.

In some embodiments, the determining a first position for each of the plurality of leaves may include obtaining a first velocity relating to the driving component; in response to a determination that the first velocity relating to the driving component is lower than a first threshold, determining the first movement direction as a backward movement direction, the each of the plurality of leaves being configured to move away from the center of the radiation field along the backward movement direction; and in response to a determination that the first velocity relating to the driving component is greater than a second threshold, determining the first movement direction as a forward movement direction, the each of the plurality of leaves being configured to move toward the center of the radiation field along the forward movement direction.

In some embodiments, the determining a target position of the each of the plurality of leaves based on the offset value may include subtracting the offset value from a preprogrammed position of the each of the plurality of leaves.

In some embodiments, the information associated with the first position may include a first main encoder value, and the determining an offset value associated with the first position based on the first angle and the first movement direction may include obtaining a first reference offset value associated with the first position of the each of the plurality of leaves from a pre-determined offset table; obtaining a first main encoder value corresponding to the first position of the each of the plurality of leaves, the first main encoder value being acquired by the main encoder; obtaining a second main encoder value corresponding to a second position of the each of the plurality of leaves, the second main encoder value being acquired by the main encoder, and the second position being a position at where a movement direction of the each of the plurality of leaves changes from a second movement direction to the first movement direction; and determining the offset value associated with the first position based on the first movement direction, the first reference offset value, and a difference between the first main encoder value and the second main encoder value.

In some embodiments, the determining the offset value associated with the first position based on the first movement direction, the first reference offset value, and a difference between the first main encoder value and the second main encoder value may include if the each of the plurality of leaves moves away from the center of the radiation field along the first movement direction, designating a minimum value between the first reference offset value and a sum of the difference between the first main encoder value and the second main encoder value and a second reference offset value associated with the second position as the offset value associated with the first position; and if the each of the plurality of leaves moves toward the center of the radiation field along the first movement direction, designating a maximum value between the first reference offset value and a sum of the second reference offset value associated with the second position and the difference between the first main encoder value and the second main encoder value as the offset value associated with the first position.

In some embodiments, the determining an offset value associated with the first position based on the first angle and the first movement direction may include if the each of the plurality of leaves moves toward the center of the radiation field along the first movement direction and the first angle is equal to 0 degrees, designating the offset value associated with the first position as 0.

In some embodiments, the determining a target position of the each of the plurality of leaves based on the offset value may include obtaining a first main encoder value corresponding to a first position of each of the plurality of leaves acquired by the main encoder; and correcting the first main encoder value based on the offset value to obtain the target position of the each of the plurality of leaves.

In some embodiments, the correcting the first main encoder value based on the offset value may include adding the offset value to the first main encoder value to obtain the target position of the each of the plurality of leaves.

According to an aspect of the present disclosure, a method for correcting position error of a leaf is provided. The method may be implemented on at least one machine each of which has at least one processor and storage. The method may include determining a first position for each of the plurality of leaves, information associated with the first position including a first movement phase, wherein a movement of the each of the plurality of leaves moves in the first movement phase is configured to move toward or away from a center of the radiation field; determining an offset value associated with the first position based on the first movement phase; and determining a target position of the each of the plurality of leaves based on the offset value.

According to an aspect of the present disclosure, a system for correcting position errors for a multi-leaf collimator (MLC) is provided. The MLC may include a plurality of leaves to shape a radiation field, each of the plurality of leaves being associated with a driving component including a main encoder. The system may include at least one storage device storing executable instructions, and at least one processor in communication with the at least one storage device, when executing the executable instructions, causing the system to determine a first position for each of the plurality of leaves, information associated with the first position including a first movement direction and a first angle, wherein the each of the plurality of leaves moves toward or away from a center of the radiation field along the first movement direction; determine an offset value associated with the first position based on the first angle and the first movement direction; and determine a target position of the each of the plurality of leaves based on the offset value.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 14A is a schematic diagram illustrating an exemplary gantry of the radiotherapy device 110 in a sectional view according to some embodiments of the present disclosure;

FIG. 14B-FIG. 14C are schematic diagrams illustrating exemplary leaves of a multi-leaf collimator in a sectional view according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 3:
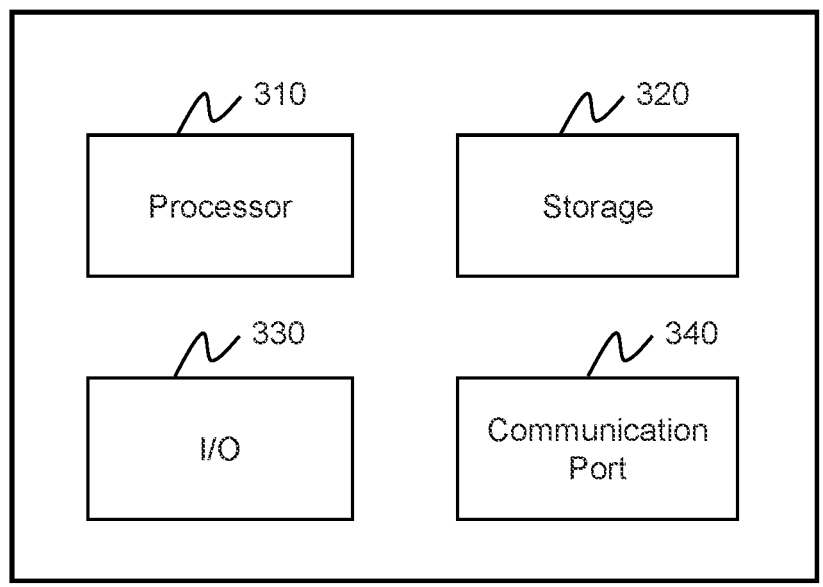
FIG. 3 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Provided herein are systems and components for medical diagnostic and/or treatment. In some embodiments, the diagnostic and treatment system may include a radiotherapy system. The radiotherapy system may include a treatment plan system (TPS), an image-guided radiotherapy (IGRT) system, etc. Merely by way of example, the image-guided radiotherapy (IGRT) system may include, for example, a CT guided radiotherapy system, an MRI guided radiotherapy system, etc.

An aspect of the present disclosure relates to a system and method for correcting position errors of a multi-leaf collimator (MLC) including a plurality of leaves to scale a radiation field. For each of the plurality of leaves, the system may determine a current position denoted by a first movement direction and a first angle. The movement of each of the plurality of leaves along the first movement direction may be configured to expand or narrow the radiation field. Then, an offset value associated with the current position of the each of the plurality of leaves may be determined based on the first angle of the each of the plurality of leaves and the first movement direction of the each of the plurality of leaves. Further, a target position of the each of the plurality of leaves may be determined according to the offset value and the first movement direction of the leaf.

It should be noted that the radiotherapy system 100 described below is merely provided for illustration purposes, and not intended to limit the scope of the present disclosure. For persons having ordinary skills in the art, a certain amount of variations, changes, and/or modifications may be deducted under the guidance of the present disclosure. Those variations, changes, and/or modifications do not depart from the scope of the present disclosure.

Figure 1:
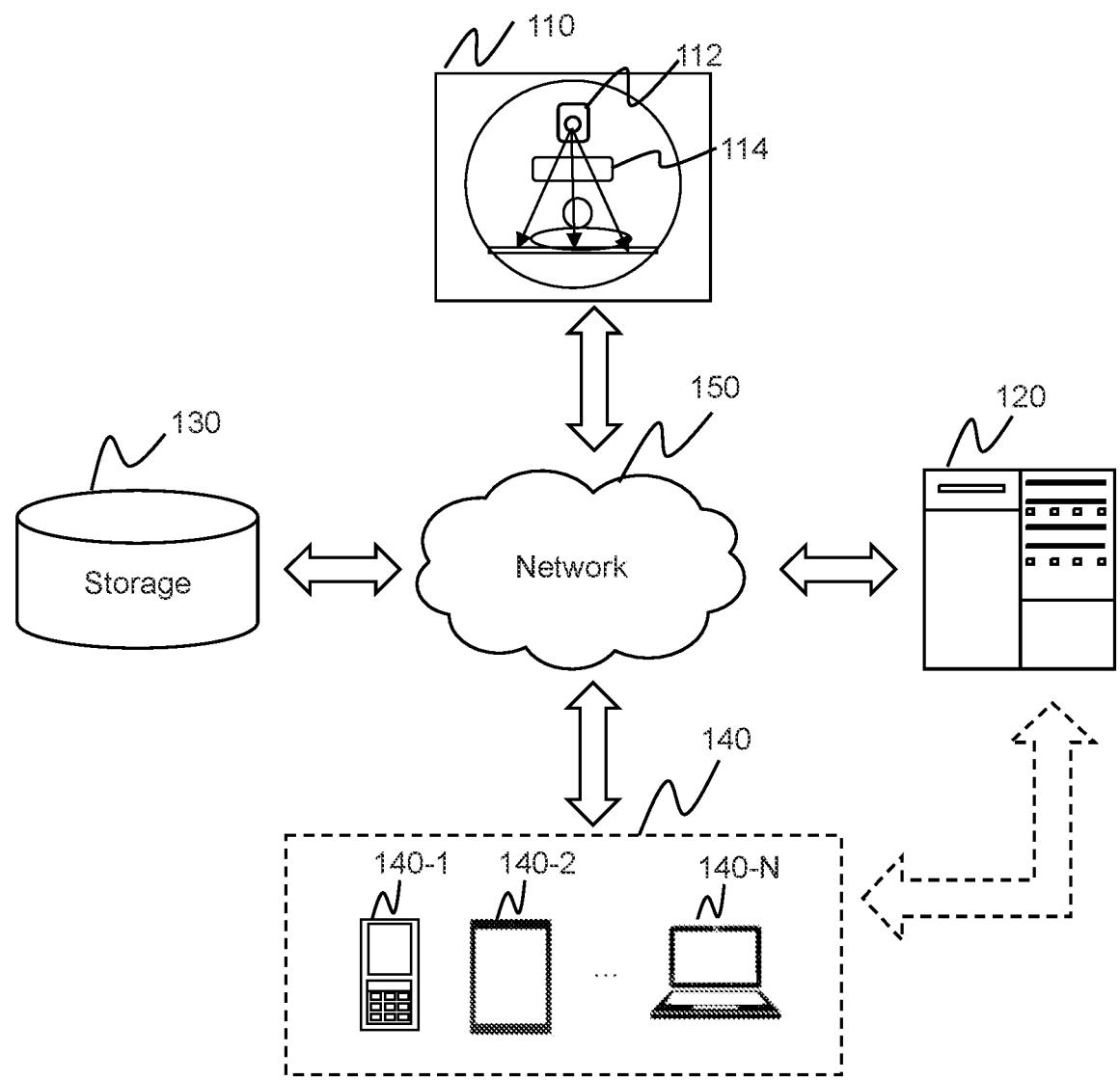
FIG. 1 is a schematic diagram illustrating an exemplary radiotherapy system according to some embodiments of the present disclosure.

FIG. 1 is a schematic diagram illustrating an exemplary radiotherapy system 100 according to some embodiments of the present disclosure. As shown, the radiotherapy system 100 may include a radiotherapy device 110, a processing device 120, storage device 130, one or more terminal(s) 140, and a network 150. In some embodiments, the radiotherapy device 110, the processing device 120, the storage device 130, and/or the terminal(s) 140 may be connected to and/or communicate with each other via a wireless connection (e.g., the network 150), a wired connection, or a combination thereof. The connections between the components in the radiotherapy system 100 may vary. Merely by way of example, the radiotherapy device 110 may be connected to the processing device 120 through the network 150, as illustrated in FIG. 1. As another example, the radiotherapy device 110 may be connected to the processing device 120 directly. As a further example, the storage device 130 may be connected to the processing device 120 through the network 150, as illustrated in FIG. 1, or connected to the processing device 120 directly. As still a further example, the terminal(s) 140 may be connected to the processing device 120 through the network 150, as illustrated in FIG. 1, or connected to the processing device 120 directly (as indicated by the bidirectional arrow in the dashed line shown in FIG. 1), or connected to the radiotherapy device 110 directly or through the network 150. The terminal(s) 140 may be omitted.

The radiotherapy device 110 may perform radiotherapy treatment on at least one part of a subject. In some embodiments, the radiotherapy device 110 may include a single modality apparatus, for example, an X-ray therapy apparatus, a Co-60 teletherapy apparatus, a medical electron accelerator, etc. In some embodiments, the radiotherapy device 110 may be a multi-modality (e.g., two-modality) apparatus to acquire a medical image relating to the at least one part of the subject and perform radiotherapy treatment on the at least one part of the subject.

The subject may be biological or non-biological. For example, the subject may include a patient, a man-made object, etc. As another example, the subject may include a specific portion, organ, and/or tissue of the patient. For example, the subject may include head, neck, thorax, cardiac, stomach, blood vessel, soft tissue, tumor, nodules, or the like, or a combination thereof. In some embodiments, the subject may include a region of interest (ROI), such as a tumor, a node, etc.

In some embodiments, the radiotherapy device 110 may include a gantry to which a treatment head may be connected. The treatment head may include a radiation source 112 and a multi-leaf collimator (MLC) 114. The radiation source 112 may emit radiation beams to a subject. The MLC 114 may be configured to collimate radiation beams emitted from the radiation source 112. In some embodiments, the MLC 114 may include a plurality of leaves to shape a radiation field. The plurality of leaves may be driven by one or more driving components (e.g., motors) to move to specific positions to expand or narrow the radiation field. Due to the mechanical factors associated with the one or more driving components (e.g., motors), an actual position of a leaf may be inconsistent with an ideal position specified by the processing device 120, which causes a position error between the actual position and the ideal position. The position error of a leaf may be caused by the backlash error relating to a driving component, leaf deformation, leaf positioning, horizontality, perpendicularity, or the like, or a combination thereof.

In some embodiments, the driving component may include a main encoder configured to acquire a position of a leaf driven by the driving component. The main encoder may be used to determine the position of the leaf based on a parameter (e.g., a rotation velocity, a rotation count, etc.) of the driving component (e.g., a motor). For example, if the diving component drives a leaf to move via rotations of a motor, the main encoder may be configured to acquire a rotation count of the motor. Then, the position of the leaf may be determined based on the rotation count of the motor. In some embodiments, the main encoder may include an encoder of the motor (also referred to as motor encoder), a potentiometer mounted on the shaft end of the motor, or any other position measurement device. In some embodiments, each of the plurality of leaves in the MLC 114 may be coupled with an auxiliary encoder. In some embodiments, the auxiliary encoder may include a grating-rule displacement sensor, a Hall sensor, a potentiometer or any other position measurement device. More descriptions of the position measurement device may be found, for example, Chinese Application No. 201510581866.0, the contents of which are hereby incorporated by reference. More descriptions of the MLC 114 may be found elsewhere in the present disclosure (e.g., FIG. 2 and the descriptions thereof).

The processing device 120 may process data and/or information obtained from the radiotherapy device 110, the storage device 130, and/or the terminal(s) 140. For example, the processing device 120 may determine a movement direction of a leaf in the MLC 114. As another example, the processing device 120 may determine an angle of each of a plurality of leaves based on an angle of the gantry of the radiotherapy device 110 and an angle of a collimator. As a further example, the processing device 120 may determine an offset value of each of a plurality of leaves in the MLC 114, and determine a position of the each of a plurality of leaves in the MLC 114 according to the determined offset value.

In some embodiments, the processing device 120 may be a single server or a server group. The server group may be centralized or distributed. In some embodiments, the processing device 120 may be local or remote. For example, the processing device 120 may access information and/or data from the radiotherapy device 110, the storage device 130, and/or the terminal(s) 140 via the network 150. As another example, the processing device 120 may be directly connected to the radiotherapy device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a mobile device 400 having one or more components as described in connection with FIG. 4.

The storage device 130 may store data, instructions, and/or any other information. In some embodiments, the storage device 130 may store data obtained from the radiotherapy device 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the radiotherapy system 100 (e.g., the processing device 120, the terminal(s) 140, etc.). One or more components in the radiotherapy system 100 may access the data or instructions stored in the storage device 130 via the network 150. In some embodiments, the storage device 130 may be part of the processing device 120.

The terminal(s) 140 may be connected to and/or communicate with the radiotherapy device 110, the processing device 120, and/or the storage device 130. For example, the terminal(s) 140 may obtain a processed image from the processing device 120. As another example, the terminal(s) 140 may obtain image data acquired via the radiotherapy device 110 and transmit the image data to the processing device 120 to be processed. In some embodiments, the terminal(s) 140 may include a mobile device 140-1, a tablet computer 140-2, ..., a laptop computer 140-N, or the like, or any combination thereof. For example, the mobile device 140-1 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120.

The network 150 may include any suitable network that can facilitate the exchange of information and/or data for the radiotherapy system 100. In some embodiments, one or more components of the radiotherapy system 100 (e.g., the radiotherapy device 110, the processing device 120, the storage device 130, the terminal(s) 140, etc.) may communicate information and/or data with one or more other components of the radiotherapy system 100 via the network 150. For example, the processing device 120 may obtain image data from the radiotherapy device 110 via the network 150. As another example, the processing device 120 may obtain user instruction(s) from the terminal(s) 140 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, switches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the radiotherapy system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 130 may be a data storage including cloud computing platforms, such as public cloud, private cloud, community, and hybrid clouds, etc. As another example, the radiotherapy system 100 may further include a treatment planning system. However, those variations and modifications do not depart the scope of the present disclosure.

Figure 2A:
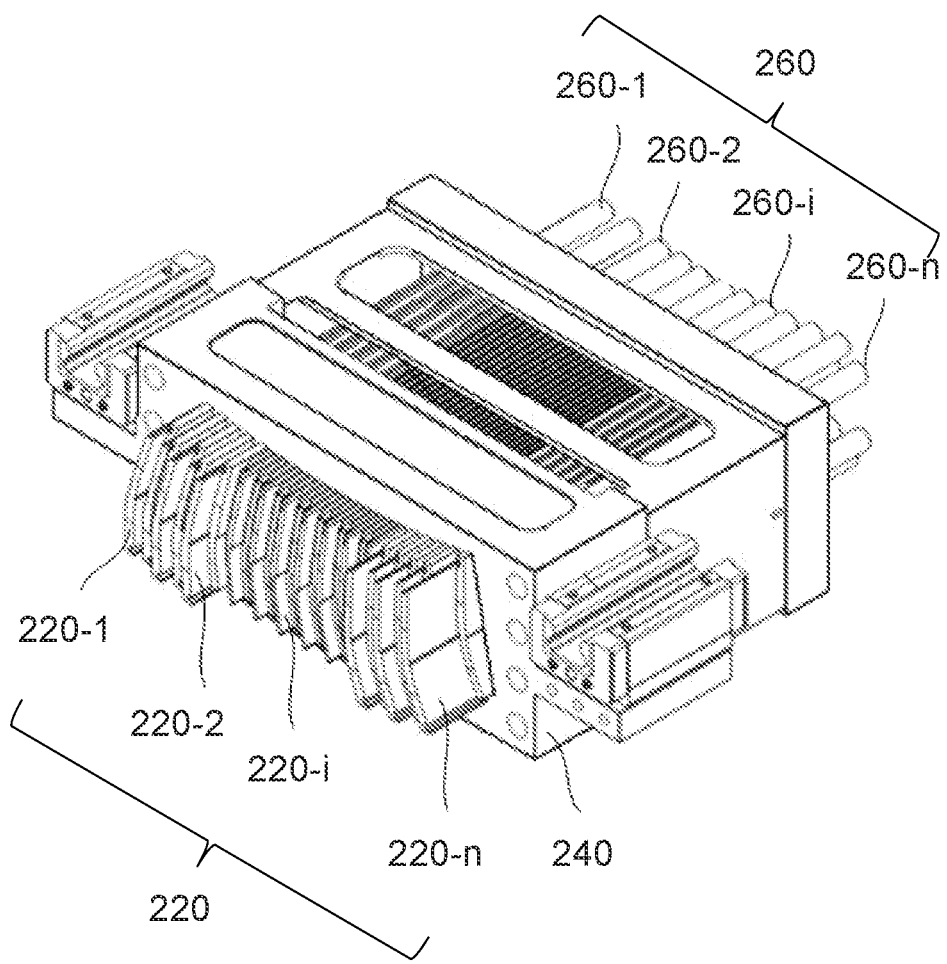
FIG. 2A is a schematic diagram illustrating an exemplary multi-leaf collimator (MLC) according to some embodiments of the present disclosure.

FIG. 2A is a schematic diagram illustrating an exemplary multi-leaf collimator (MLC) 200 according to some embodiments of the present disclosure. As shown in FIG. 2A, the MLC 200 may include a leaf assembly 220 including multiple leaves (e.g., a leaf 220-1, a leaf 220-2, a leaf 220-$i$, ..., a leaf 220-$n$, etc.), a carriage 240, and a driving assembly 260. Each of the multiple leaves may move in the carriage 240 independently, for example, move toward the center of a radiation field or move away from the center of the radiation field. The center of the radiation field may be a geometric center of the radiation field formed by the multiple leaves. The driving assembly 260 may include multiple motors (e.g., a motor 260-1, a motor 260-2, a motor 260-$i$, ..., a motor 260-$n$, etc.) associated with the multiple leaves (e.g., the leaf 220-1, the leaf 220-2, the leaf 220-$i$, ..., the leaf 220-$n$, etc.). Each of the multiple motors (e.g., the motor 260-1, the motor 260-2, the motor 260-$i$, ..., the motor 260-$n$, etc.) may drive a corresponding leaf of the multiple leaves (e.g., the leaf 220-1, the leaf 220-2, the leaf 220-$i$, ..., the leaf 220-$n$, etc.) to move independently in the carriage 240 to form the radiation field. Each one of the multiple leaves (e.g., the leaf 220-1, the leaf 220-2, the leaf 220-$i$, ..., the leaf 220-$n$, etc.) may be driven by one of the multiple motors to move toward the center of the radiation field. Further, each one of the multiple leaves (e.g., the leaf 220-1, the leaf 220-2, the leaf 220-$i$, ..., the leaf 220-n, etc.) may be driven by one of the multiple motors to move away from the center of the radiation field.

Figure 2B:
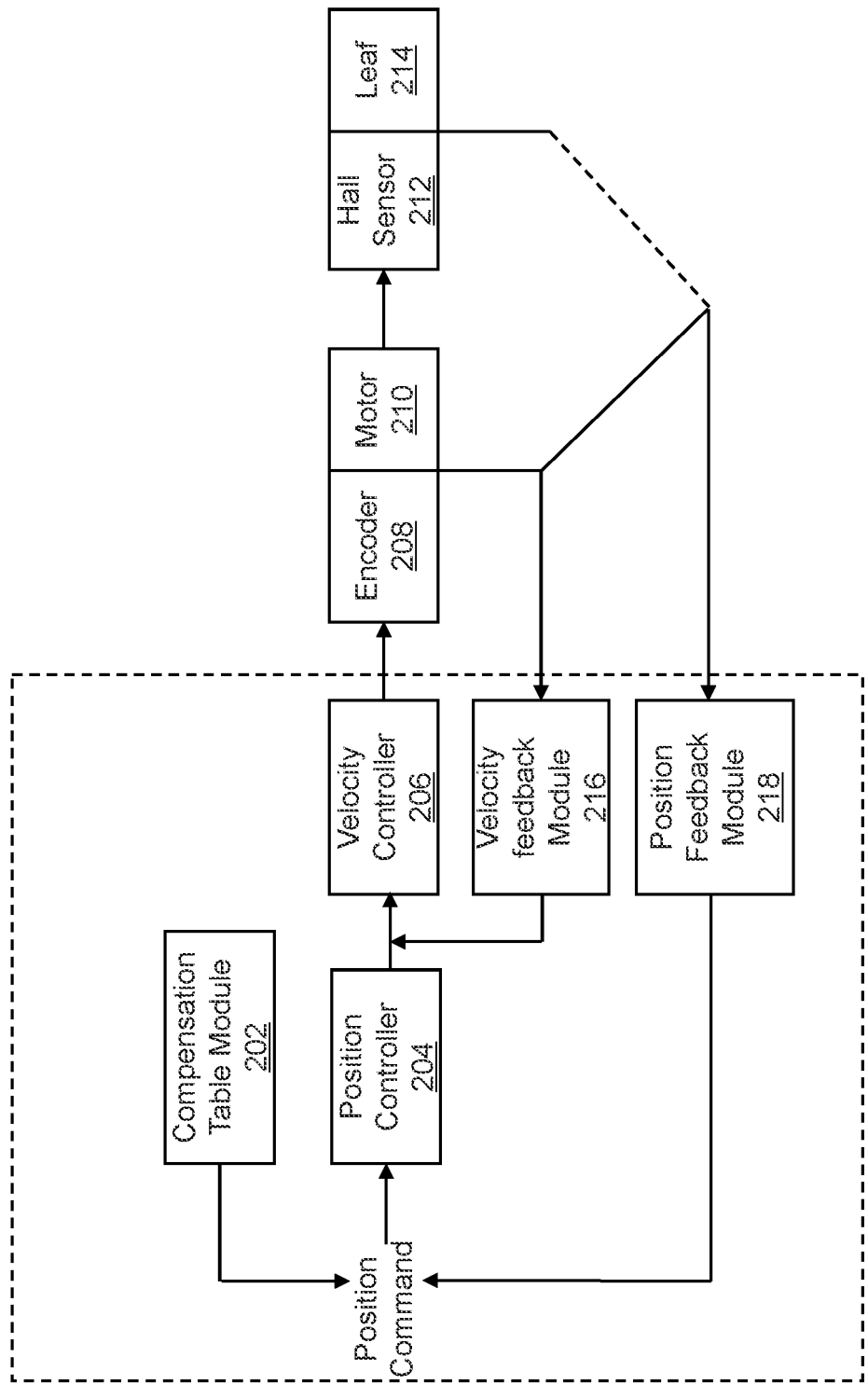
FIG. 2B is a schematic diagram illustrating an exemplary control system of a multi-leaf collimator (MLC) according to some embodiments of the present disclosure.

FIG. 2B is a schematic diagram illustrating an exemplary control system of a multi-leaf collimator (MLC) according to some embodiments of the present disclosure. As illustrated in FIG. 2B, the control system may include a compensation table module 202, a position controller 204, a velocity controller 206, a velocity feedback module 216, and a position feedback module 218.

Figure 8:
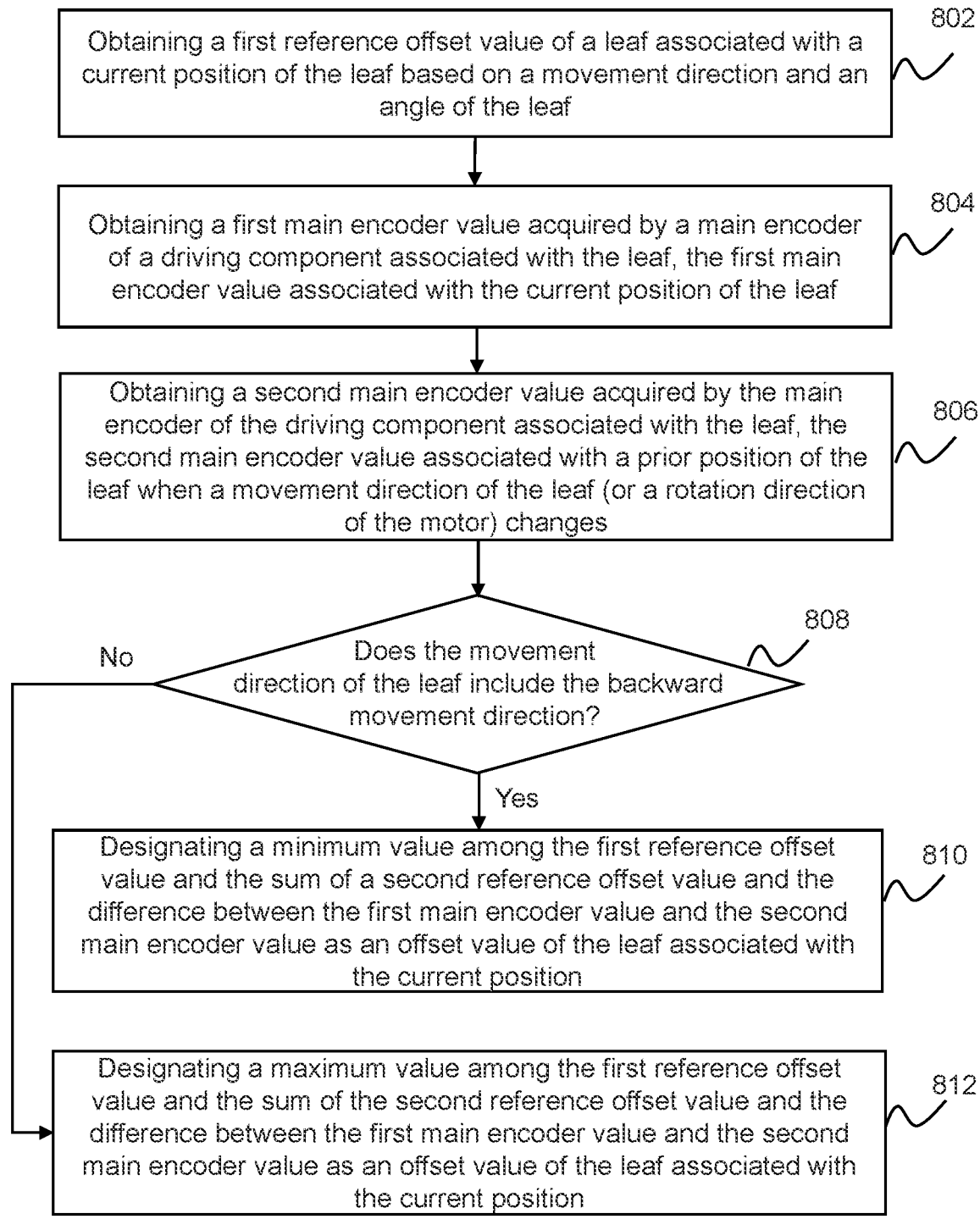
FIG. 8 is a flowchart illustrating an exemplary process for determining an offset value of a leaf based on the angle of the leaf according to some embodiments of the present disclosure.
Figure 9:
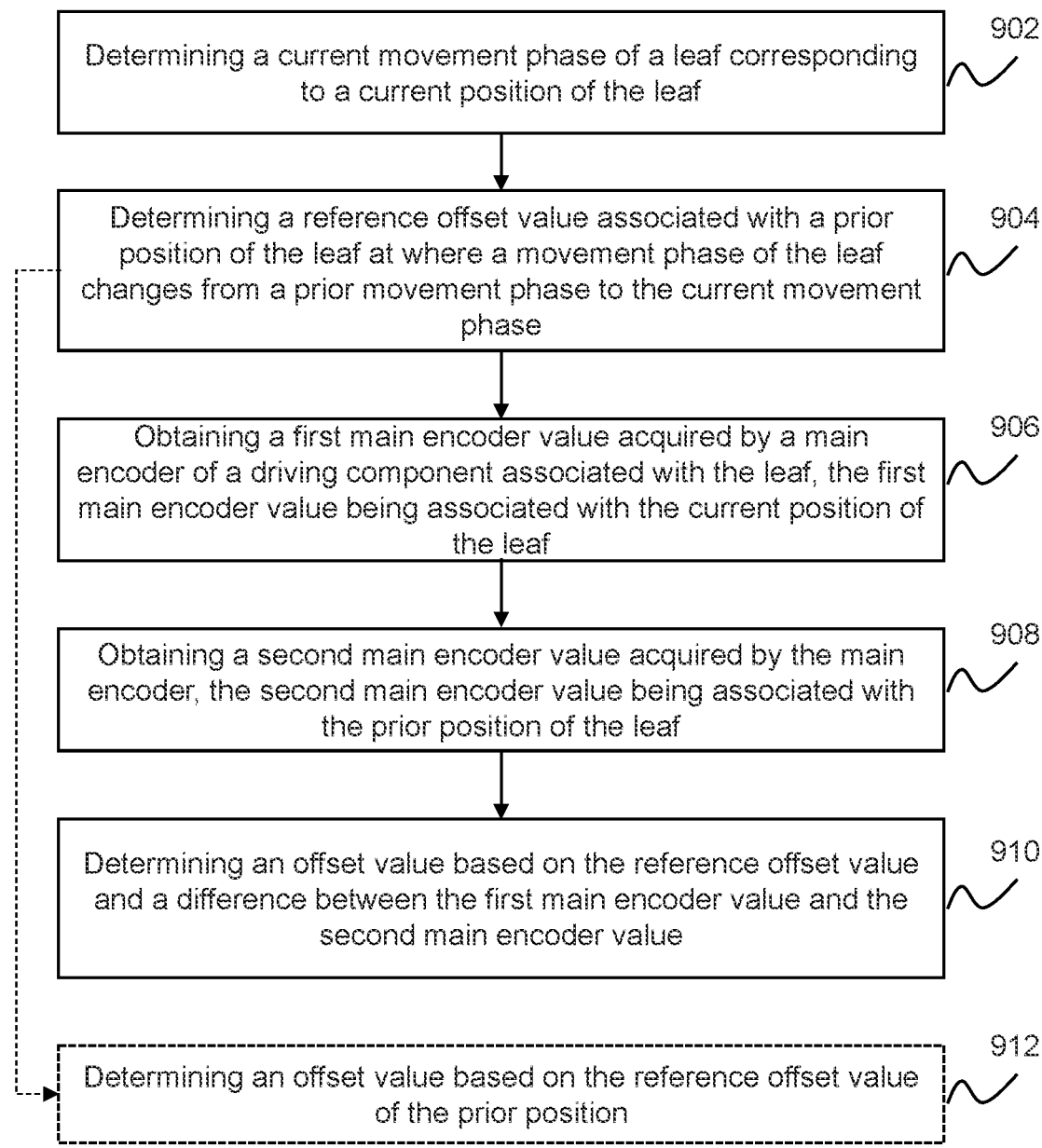
FIG. 9 is a flowchart illustrating another exemplary process for determining an offset value of a leaf based on the angle of the leaf according to some embodiments of the present disclosure.
Figure 10:
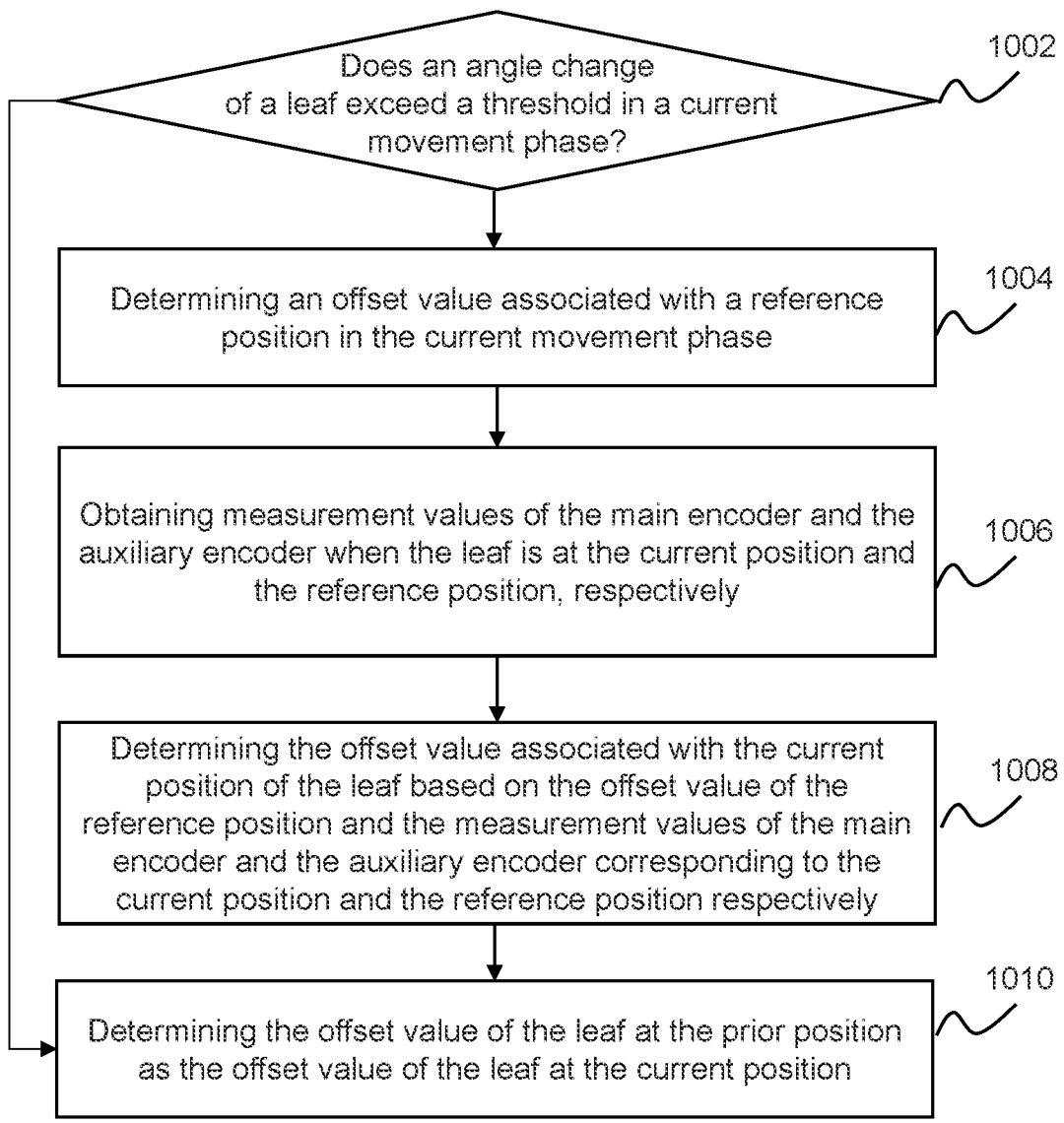
FIG. 10 is a flowchart illustrating another exemplary process for determining a reference offset value of a leaf according to some embodiments of the present disclosure.

The position controller 204 may receive a position command associated with a preprogrammed position of a leaf 214 and control the velocity controller 206 based on the position command. In some embodiments, the position command associated with the predetermined position of the leaf 214 may be modified based on an offset value associated with the leaf 214. The offset value associated with the leaf 214 may be determined by and/or obtained from the compensation table module 202 according to process 800 as illustrated in FIG. 8. In some embodiments, the offset value associated with the leaf 214 may be determined based on the current position of the leaf 214 acquired by the position feedback module 218 from an encoder 208 (or a main encoder) and/or a Hall sensor 212 (or an auxiliary encoder) according to process 900 as illustrated in FIG. 9 and/or process 1000 as illustrated in FIG. 10. The velocity controller 206 may determine a reference rotation velocity of the motor 210 based on the position command. The velocity controller 206 may control the motor 210 to rotate according to the reference rotation velocity within a certain time to drive the leaf 214 associated with the motor 210 to move to the preprogrammed position. The encoder 208 associated with the motor 210 may acquire a rotation count of the motor 210 to determine a current or real-time position of the leaf 214. The Hall sensor 212 may be coupled with the leaf 214. The Hall sensor 212 may acquire a signal relating to the current or real-time position of the leaf 214.

The velocity feedback module 216 may be connected with the encoder 208 and/or the Hall sensor 212. The velocity feedback module 216 may be configured to determine a current rotation velocity of the motor 210 based on the rotation of the motor 210 acquired by the encoder 208. Alternatively or simultaneously, the velocity feedback module 216 may be configured to determine a current movement velocity of the leaf 214 based on the signal acquired by the Hall sensor 212. The velocity controller 206 may acquire the current rotation velocity of the motor 210 and/or the current movement velocity of the leaf 214. Then, the velocity controller 206 may modify the driving force of the motor 210 based on a difference between a referenced rotation velocity and the current rotation velocity of the motor 210 and/or a difference between a reference velocity and the current movement velocity of the leaf 214.

The position feedback module 218 may be connected to the encoder 208 and/or the Hall sensor 212. The position feedback module 218 may be configured to determine a current position of the leaf 214 based on the rotation count of the motor 210 acquired by the encoder 208 and a current movement velocity of the leaf 214 based on magnetic field fluctuation signals acquired by the Hall sensor 212 (e.g., an encoder). Then, the position controller 204 may determine an offset value associated with the current position of the leaf 214 determined based on the encoder 208 and/or the Hall sensor 212. The position command may be modified based on the offset value associated with the current position of the leaf 214. More descriptions of the MLC may be found, for example, Chinese Publication No. 104667427A entitled "Leaf position monitoring device for a multi-leaf collimator (MLC), an MLC, and a radiotherapy device ( 多叶光栅的叶 片位置监测装置，多叶光 栅，放疗设备 ).", the contents of which are hereby incorporated by reference.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the compensation table module 202 may be omitted. As another example, the velocity feedback module 216 and the position feedback module 218 may be integrated into one single module. However, those variations and modifications do not depart the scope of the present disclosure.

Figure 2C:
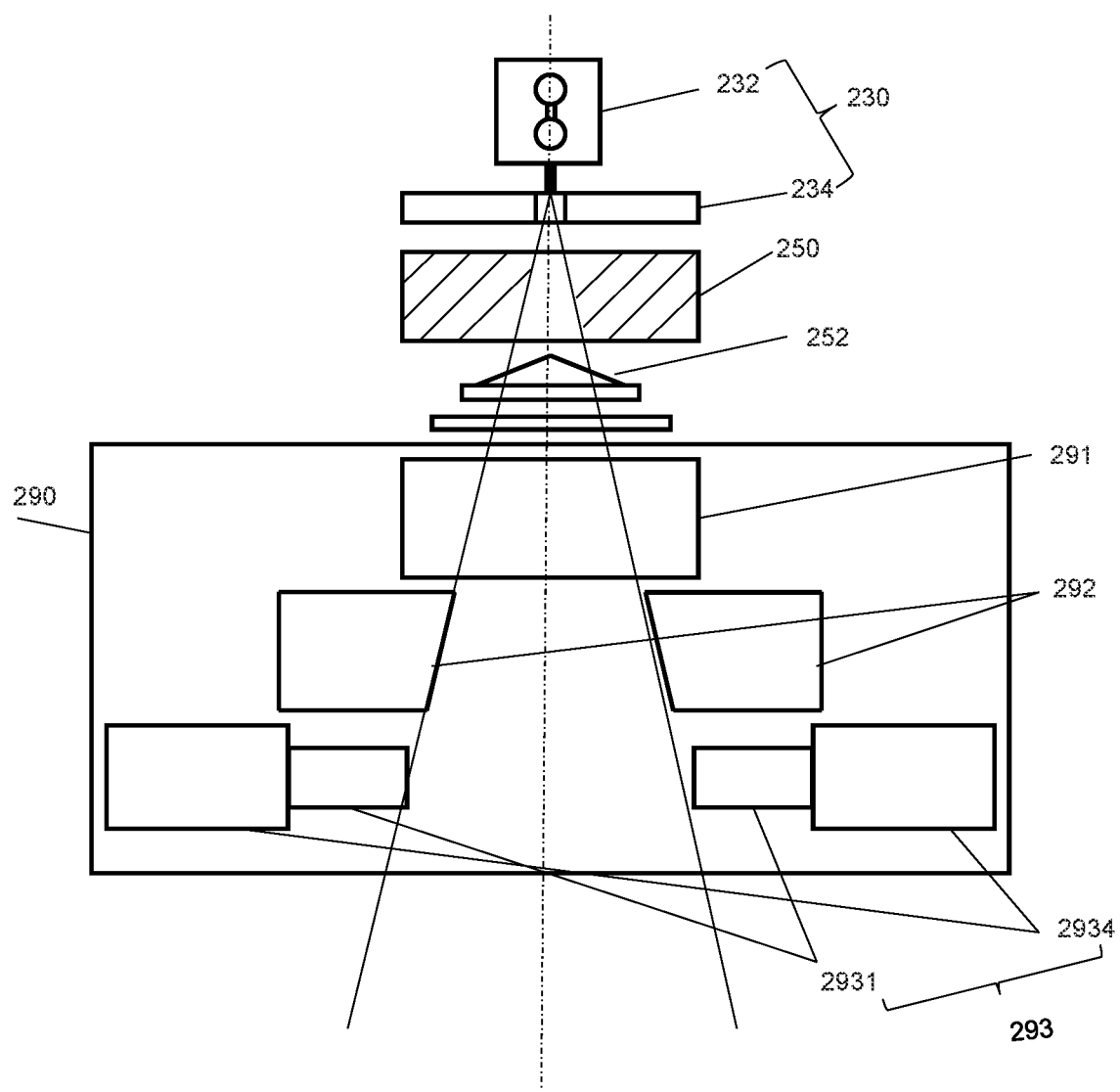
FIG. 2C is a section diagram illustrating an exemplary treatment head of a radiotherapy device according to some embodiments of the present disclosure.

FIG. 2C is a section diagram illustrating an exemplary treatment head of a radiotherapy device according to some embodiments of the present disclosure. As illustrated in FIG. 2C, the treatment head may include a radiation source 230, a primary collimator 250, one or more filters 252, a collimator 290, or any other component (e.g., a chamber between the one or more filters 252 and the collimator 290). The radiation source 230 may generate and/or emit radiation beams to a subject. The radiation source may include an accelerator 232, a target 234, or any other component (not shown). The primary collimator 250 may be configured to limit or collimate high energy beams (e.g., X-rays) emitted from the radiation source so that only those traveling parallel to a specified direction are allowed to pass through the primary collimator 250. The one or more filters 252 may be configured to adjust the distribution of the radiation impinging upon the subject. The one or more filters 252 may include a flattening filter, a bowtie filter, a wedge filter, or the like, or any combination thereof.

The collimator 290 may be configured to shape a radiation field. The collimator 290 may include a Y-JAW 291, a X-JAW 292, an MLC 293 including a leaf assembly 2931 and a carriage 2934, or any other components. The leaf assembly 2933 may include multiple leaves. The MLC 293 may also include a driving assembly (not shown). Each of the multiple leaves may move in the carriage 2934 independently, for example, move toward the center of a radiation field or move away from the center of the radiation field to shape the radiation field. The MLC 293, the Y-JAW 291, and the X-JAW 292 may be form the radiation field, cooperatively. The MLC 293 may be mounted in the collimator 290. The collimator 290 may rotate. The MLC 293 may rotate along the rotation of the collimator 290. More descriptions for the MLC 293 may be found in elsewhere in the present disclosure (e.g., FIG. 2A and the descriptions thereof).

FIG. 3 is a schematic diagram illustrating exemplary hardware and/or software components of an exemplary computing device 300 on which the processing device 120 may be implemented according to some embodiments of the present disclosure. As illustrated in FIG. 3, the computing device 300 may include a processor 310, storage 320, an input/output (I/O) 330, and a communication port 340.

The processor 310 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 310 may process data obtained from the radiotherapy device 110, the storage device 130, terminal(s) 140, and/or any other component of the radiotherapy system 100. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both operations A and B, it should be understood that operation A and operation B may also be performed by two or more different processors jointly or separately in the computing device 300 (e.g., a first processor executes operation A and a second processor executes operation B, or the first and second processors jointly execute operations A and B).

The storage 320 may store data/information obtained from the radiotherapy device 110, the storage device 130, the terminal(s) 140, and/or any other component of the radiotherapy system 100. In some embodiments, the storage 320 may include a mass storage, removable storage, a volatile read-and-write memory, a read-only memory (ROM), or the like, or a combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure.

The I/O 330 may input and/or output signals, data, information, etc. In some embodiments, the I/O 330 may enable user interaction with the processing device 120. In some embodiments, the I/O 330 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 340 may be connected to a network (e.g., the network 150) to facilitate data communications. The communication port 340 may establish connections between the processing device 120 and the radiotherapy device 110, the storage device 130, and/or the terminal(s) 140. The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 340 may be and/or include a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
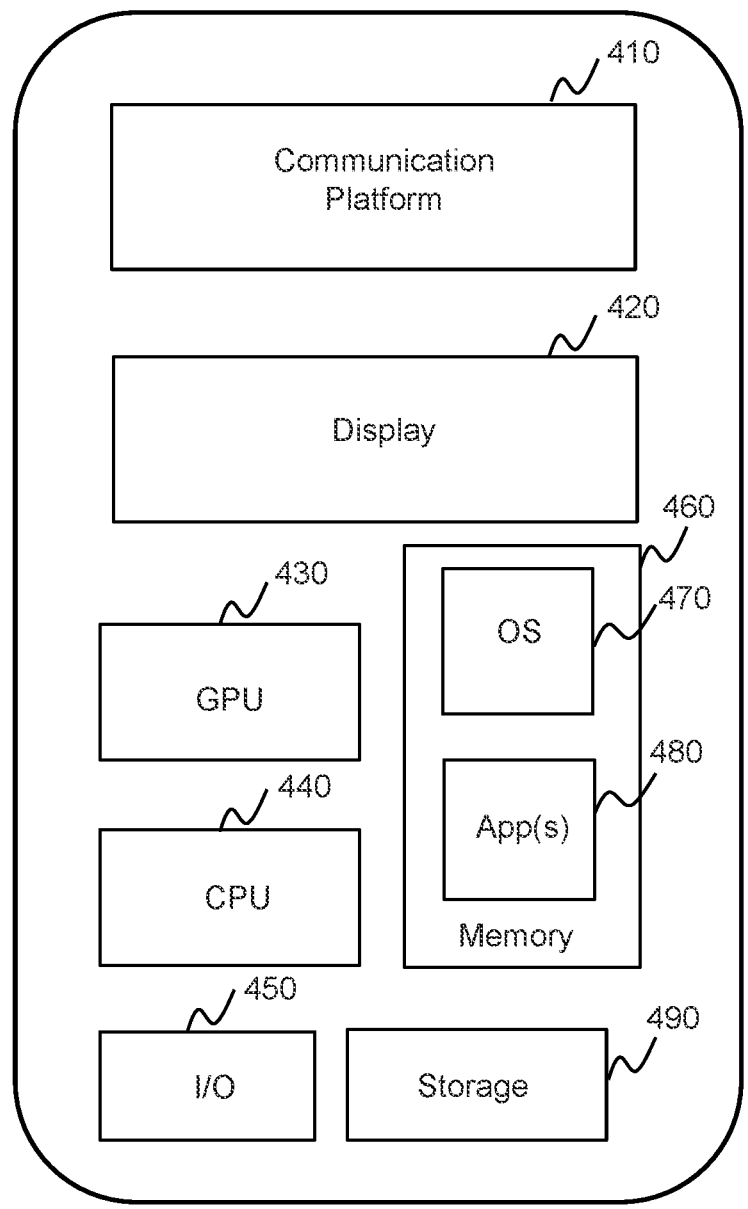
FIG. 4 is a schematic diagram illustrating exemplary hardware and/or software components of an exemplary mobile device on which the terminal(s) may be implemented according to some embodiments of the present disclosure.

FIG. 4 is a schematic diagram illustrating exemplary hardware and/or software components of an exemplary mobile device 400 on which the terminal(s) 140 may be implemented according to some embodiments of the present disclosure. As illustrated in FIG. 4, the mobile device 400 may include a communication platform 410, a display 420, a graphics processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS™, Android™, Windows Phone™, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 120. User interactions with the information stream may be achieved via the I/O 450 and provided to the processing device 120 and/or other components of the radiotherapy system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 5:
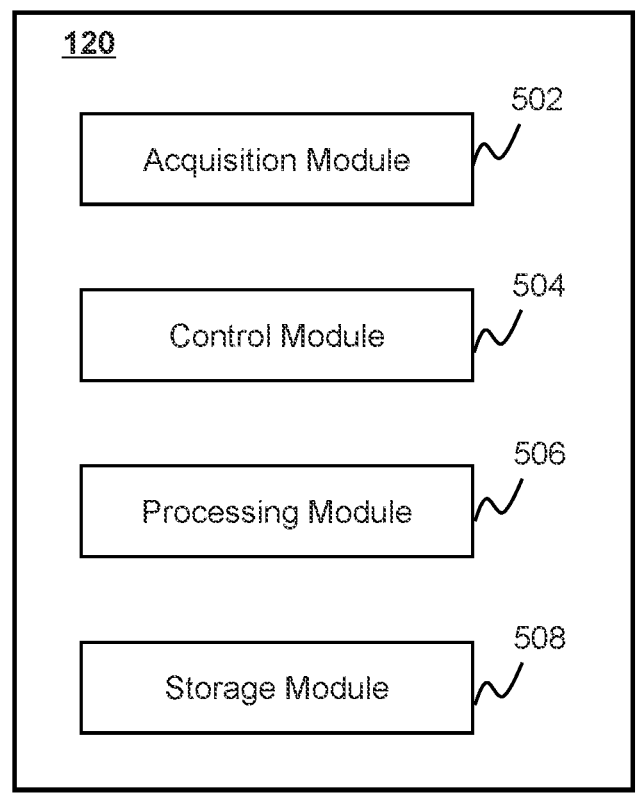
FIG. 5 is a block diagram illustrating an exemplary processing device according to some embodiments of the present disclosure.

FIG. 5 is a block diagram illustrating an exemplary processing device 120 according to some embodiments of the present disclosure. The processing device 120 may include an acquisition module 502, a control module 504, a processing module 506, and a storage module 508. At least a portion of the processing device 120 may be implemented on a computing device as illustrated in FIG. 3 or a mobile device as illustrated in FIG. 4.

The acquisition module 502 may acquire data. In some embodiments, the data may be acquired from the radiotherapy device 110, the storage device 130, and/or the terminal(s) 140. In some embodiments, the data may include parameters (e.g., an angle) relating to an MLC, movement information (e.g., movement directions, movement phases, etc.) relating to a leaf in an MLC, an offset table associated with an MLC, instructions, or the like, or a combination thereof. The instructions may be executed by the processor(s) of the processing device 120 to perform exemplary methods described in the present disclosure. In some embodiments, the acquired data may be transmitted to the processing module 506 for further processing, or stored in the storage module 508.

The control module 504 may control operations of the acquisition module 502, the processing module 506, and/or the storage module 508, for example, by generating one or more control parameters. For example, the control module 504 may control the acquisition module 502 to acquire data (e.g., an angle of an MLC, an angle of a gantry, etc.). As another example, the control module 504 may control the processing module 506 to generate an image relating to a subject. As a further example, the control module 504 may control the processing module 506 to implement a radiotherapy treatment plan for the subject. In some embodiments, the control module 504 may receive a real-time command or retrieve a preprogrammed command provided by a user (e.g., a doctor) to control one or more operations of the acquisition module 502 and/or the processing module 506. For example, the control module 504 may adjust the acquisition module 502 and/or the processing module 506 to determine the angle of a leaf according to the real-time command and/or the preprogrammed command. In some embodiments, the control module 504 may communicate with one or more other modules of the processing device 120 for exchanging information and/or data.

The processing module 506 may process data provided by various modules of the processing device 120. For example, the processing module 506 may determine an offset value for each of leaves in a collimator (e.g., a multi-collimator in the radiotherapy device 110). As another example, the processing module 506 may generate a position instruction based on the offset value for each of the leaves in the collimator (e.g., a multi-leaf collimator in the radiotherapy device 110).

The storage module 508 may store information. The information may include programs, software, algorithms, data, text, number, images, and some other information. For example, the information may include image data (e.g., a radiological image, an optical image, etc.), motion or position data (e.g., a speed, a displacement, an acceleration, a spatial position, etc.) relating to a component in the radiotherapy device 110 (e.g., the couch), instructions, or the like, or a combination thereof. In some embodiments, the storage module 508 may store program(s) and/or instruction(s) that can be executed by the processor(s) of the processing device 120 to acquire data, determine a spatial position of at least one part of a subject.

In some embodiments, one or more modules illustrated in FIG. 5 may be implemented in at least part of the radiotherapy system 100 as illustrated in FIG. 1. For example, the acquisition module 502, the control module 504, the processing module 506, and/or the storage module 508 may be integrated into a console (not shown). Via the console, a user may set parameters for scanning a subject, controlling imaging or treatment processes, controlling parameters for the reconstruction of an image, etc. In some embodiments, the console may be implemented via the processing device 120 and/or the terminal(s) 140.

Figure 6:
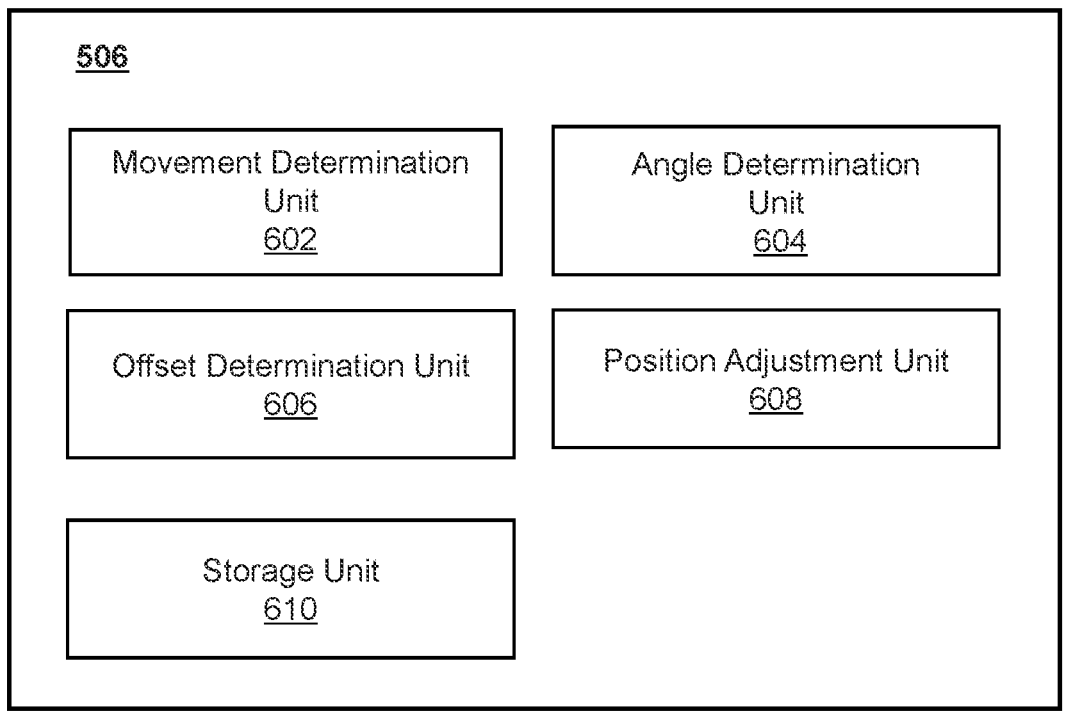
FIG. 6 is a block diagram illustrating an exemplary processing module according to some embodiments of the present disclosure.

FIG. 6 is a block diagram illustrating an exemplary processing module 506 according to some embodiments of the present disclosure. The processing module 506 may include a movement determination unit 602, an angle determination unit 604, an offset determination unit 606, a position adjustment unit 608, and a storage unit 610. At least a portion of the processing module 506 may be implemented on a computing device as illustrated in FIG. 3 or a mobile device as illustrated in FIG. 4.

The movement determination unit 602 may be configured to determine a movement direction or a movement phase of the leaf. In some embodiments, the movement determination unit 602 may determine the movement direction or movement phase of the leaf based on the measurements of a main encoder (e.g., a motor encoder) connected with a driving component and/or an auxiliary encoder (e.g., a Hall sensor) associated with the leaf. For example, when an initial phase is an unknown phase, and the movement determination unit 602 may obtain a first measurement value and a second measurement value of the leaf through the Hall sensor in two adjacent sampling periods. If the difference between the first measurement value and the second measurement value is larger than a first preprogrammed count (e.g., 2 count, etc.), the leaf may be determined in a forward movement phase. If the difference between the first measurement value and the second measurement value is less than a second preprogrammed count (e.g., 0 count, etc.), then the leaf may be determined in a backward movement phase. In some embodiments, the movement determination unit 602 may be configured to determine a movement direction or a movement phase of the leaf based on a velocity of the leaf and/or a driving component associated with the leaf. For example, if the velocity of the driving component is less than a velocity threshold, the leaf may move away from the center of a radiation field.

The angle determination unit 604 may be configured to determine an angle of the leaf. In some embodiments, the angle of the leaf may be determined by the angle determination unit 604 based on an angle of the gantry and an angle of a collimator. The collimator may be configured to support the MLC. More descriptions of the determining the angle of the leaf based on the angle of the gantry and the angle of the collimator may be found in operation 704 and the descriptions thereof.

The offset determination unit 606 may be configured to determine the target offset of the leaf. In some embodiments, the offset determination unit 606 may determine the offset value of the leaf based on a preprogrammed offset table. In some embodiments, the offset value of the leaf may be determined based on measurement values acquired by a main encoder of a driving component associated with the leaf and an auxiliary encoder associated with the leaf.

The position adjustment unit 608 may be configured to adjust the position of the leaf. In some embodiments, the position adjustment unit 608 may determine a target position of the leaf based on the offset value determined by the offset determination unit 606 associated with the position of the leaf. Further, the target position of the leaf may be determined by subtracting the offset value from a preprogrammed position of the leaf. The preprogrammed position of the leaf may be set by a user via the terminal device 140, or according to a default setting of the radiotherapy system 100, such as a treatment plan of a subject. In some embodiments, the position adjustment unit 608 may determine an actual position of the leaf based on the offset value determined by the offset determination unit 606 associated with the position of the leaf. Further, the actual position of the leaf based on the offset value determined by summing the current position of the leaf and the offset value. The current position of the leaf may be determined using the main encoder.

The storage unit 610 may store information relating to, for example, determining the reference offset value, adjusting the position of the leaf, etc. The information may include programs, software, algorithms, data, text, number, and some other information. In some embodiments, the information relating to determining the reference offset may include data for determining the reference offset, algorithms for determining the reference offset value, parameters for determining the reference offset value, etc. The storage unit 610 may be a memory that stores data to be processed by processing devices, such as CPUs, GPUs, etc. In some embodiments, the storage unit 610 may be a memory that may be accessible by one or more GPUs or maybe a memory that is only accessible by a specific GPU.

It should be noted that the above description of the processing module 506 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, the movement determination unit 602 and the angle determination unit 604 may be integrated into one single unit.

Figure 7:
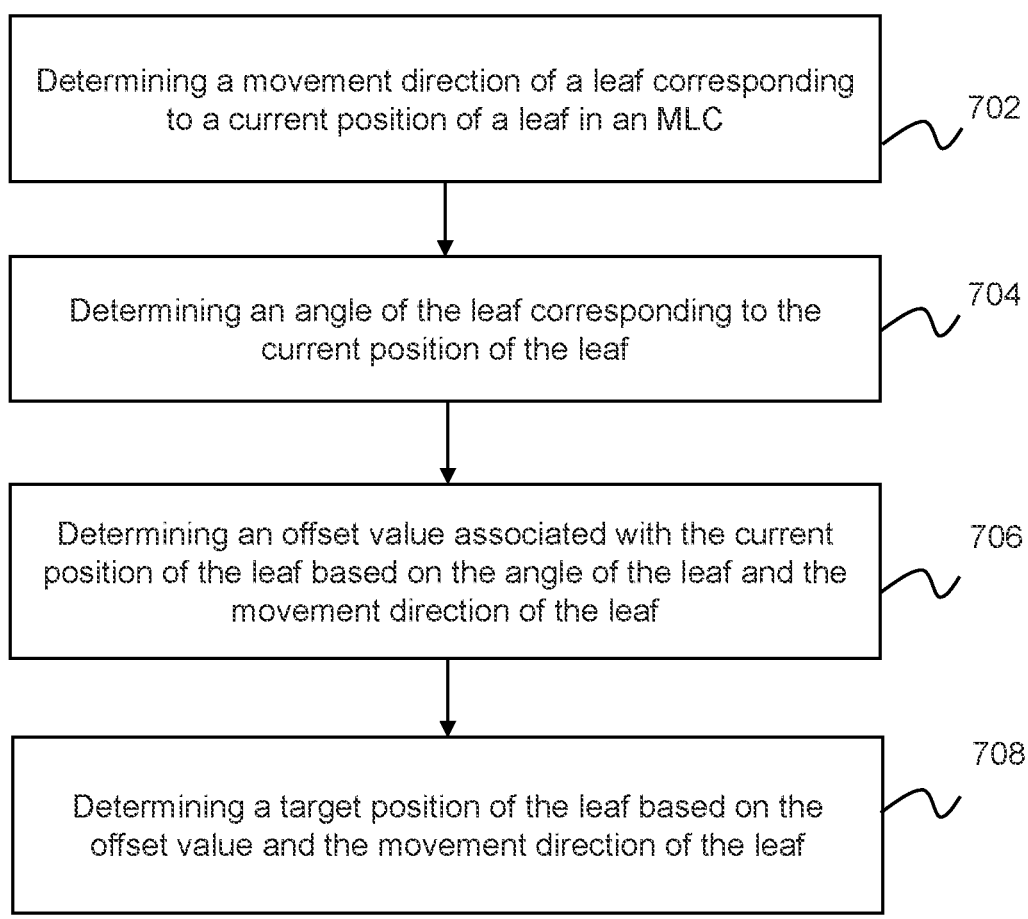
FIG. 7 is a flowchart illustrating an exemplary process for correcting a target position of a leaf according to some embodiments of the present disclosure.

FIG. 7 is a flowchart illustrating an exemplary process 700 for determining a target position of a leaf according to some embodiments of the present disclosure. In some embodiments, one or more operations of process 700 illustrated in FIG. 7 may be implemented in the radiotherapy system 100 illustrated in FIG. 1. For example, the process 700 illustrated in FIG. 7 may be stored in the storage device 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4).

In 702, a movement direction of a leaf corresponding to a current position of the leaf in a multi-leaf collimator (MLC) may be determined. Operation 702 may be performed by the processing module 506. As used herein, the current position may be also referred to as a first position. In some embodiments, the movement direction of the leaf may include one of a backward movement direction and a forward movement direction. As used herein, the movement direction of a leaf may be considered as the backward movement direction if the leaf moves away from the center of a radiation field. The movement direction of a leaf may be considered to as the forward movement direction if the leaf moves toward the radiation field. In some embodiments, the movement direction of the leaf may correspond to a current or real-time movement direction when the leaf is at the current position. In some embodiments, the movement direction of the leaf may correspond to a preprogrammed movement direction of the leaf. The preprogrammed movement direction of the leaf may be determined based on an initial position of the leaf and a preprogrammed position of the leaf in a radiotherapy planning associated with the MLC. As used herein, the preprogrammed position of the leaf may refer to a default (or a commanded) position defined by a main encoder in the driving component. The preprogrammed position of the leaf may be set by a user via the terminal device 140, or according to a default setting of the radiotherapy system 100, such as a treatment plan associated with the MLC.

In some embodiments, the movement direction of the leaf may be determined based on a rotation direction of a motor associated with the leaf in the driving component of the MLC. In some embodiments, the rotation direction of the motor may include one of a first rotation direction and a second rotation direction. When the motor rotates with the first rotation direction (e.g., a clockwise direction or anti-clockwise direction), the rotation of the motor may cause the leaf to move away from the center of the radiation field (i.e., with the backward movement direction). When the motor rotates with the second rotation direction (e.g., a clockwise direction or anti-clockwise direction), the rotation of the motor may cause the leaf to move toward the center of the radiation field (i.e., with the forward movement direction).

In some embodiments, the rotation direction of the motor may be determined based on a rotation velocity of the motor when the leaf is at the current position. Further, if the rotation velocity of the motor is less than a first velocity threshold, the rotation direction of the motor may be determined as the first rotation direction. If the rotation velocity of the motor is greater than a second velocity threshold, the rotation direction of the motor may be determined as the second rotation direction. In some embodiments, the rotation velocity of the motor may be preprogrammed based on the preprogrammed position of the leaf. In some embodiments, the rotation velocity of the motor may be a current or real-time rotation velocity determined based on an encoder value acquired by a main encoder associated with the motor when the leaf is at the current position. For example, in adjacent sampling periods (also referred to as adjacent calculation cycles) of the main encoder, two measurements may be acquired by the main encoder corresponding two different positions of the leaf. The rotation velocity of the motor may be determined based on the two measurements and the sampling period.

In some embodiments, the rotation direction of the motor may be determined based on the preprogrammed position of the leaf and the current position of the leaf. For example, if a distance between the preprogrammed position of the leaf and a reference point (e.g., the front end A of the MLC 200 as shown in FIG. 2A) is greater than a distance between the current position of the leaf and the reference point, the rotation direction of the motor may cause the leaf to move toward the preprogrammed position, i.e., move toward the center of the radiation field. If the distance between the preprogrammed position of the leaf and the reference point is less than the distance between the current position of the leaf and the reference point, the rotation direction of the motor may cause the leaf to move toward the preprogrammed position, i.e., move away from the center of the radiation field. The first velocity threshold may be a constant lower than or equal to zero, and the second velocity threshold may be a constant equal to or greater than zero. The first velocity threshold and/or the second velocity threshold may be determined by a user or according to a default setting of the radiotherapy system 100.

In 704, an angle of the leaf corresponding to the current position of the leaf may be determined. Operation 704 may be performed by the angle determination unit 604. The angle of the leaf may be determined based on an angle of a collimator for supporting the MLC (e.g., the MLC 114) and an angle of a gantry of a radiotherapy device (e.g., the radiotherapy device 110) including the MLC. The MLC may be mounted on the collimator and rotate with the collimator. Further, the angle of the leaf may be determined according to Equation (1) as described below:

$$\sin(\alpha)=\sin(\beta)*\cos(\theta) \quad (1)$$

where, α represents an angle of a leaf; β represents an angle of a gantry of a radiotherapy device, and θ represents an angle of a collimator in the gantry of the radiotherapy device. As used herein, an angle of a leaf, an angle of a gantry of a radiotherapy device, and an angle of a collimator may be described in the coordinate systems of IEC (International Electrotechnical Commission) specifications.

According to Equation (1), when the angle of the gantry is 0 degrees and the angle of the collimator is 90 degrees, the angle of the leaf may be determined to be 0 degrees. When the angle of the gantry is 90 degrees and the angle of the collimator is 0 degrees, the angle of the leaf may be determined to be 90 degrees. When the angle of the gantry is 45 degrees and the angle of the collimator is 45 degrees, the angle of the leaf may be determined to be 30 degrees. In some embodiments, the angle of the gantry and the angle of the MLC may be determined according to a default setting of the radiotherapy system 100, such as a treatment planning associated with the radiotherapy system 100. In some embodiments, the angle of the gantry and the angle of the collimator may be obtained from a control system associated with the collimator. In some embodiments, the angle of the gantry and the angle of the collimator may be determined using a measurement device, for example, an angle sensor associated with the gantry and/or the collimator.

In 706, an offset value of the leaf may be determined based on the angle of the leaf and the movement direction of the leaf. Operation 706 may be performed by the offset determination unit 606. In some embodiments, a reference offset value of the leaf may be determined based on the angle of the leaf and the movement direction of the leaf. The offset value of the leaf may be determined based on a reference offset value. The reference offset value may obtain from an offset table (e.g., the Offset Table 1 as described in FIG. 8) associated with the MLC. In some embodiments, the offset table may include a plurality of reference offset values associated with each of a plurality of leaves under different angles and/or different movement directions. For example, each of the plurality of reference offset values of each of the plurality of leaves may be determined based on angles and movement directions of each of the plurality of leaves in the MLC using a distance measurement device and a main encoder of the driving component (e.g., a motor) associated with the each of the plurality of leaves. The distance measurement device may include a laser sensor, a dial indicator, a dial-gauge, etc. In some embodiments, the offset table may include a plurality of reference offset values associated with each of a plurality of leaves under different angles, different movement directions, and different positions. For example, each of the plurality of reference offset values may be determined based on angles, movement directions, and/or positions of each of a plurality of leaves in the MLC using a laser sensor and a main encoder of the driving component (e.g., a motor) associated with the each of the plurality of leaves. A reference offset value corresponding to the leaf may be determined from the offset table according to the movement direction of the leaf determined in 702, the angle of the leaf determined in 704, and/or the current position of the leaf described in 702. Then, the offset value of the leaf may be determined based on the reference offset value corresponding to the leaf. More descriptions for determining the offset value of the leaf based on the offset table may be found in FIG. 8, and the descriptions thereof.

In some embodiments, the offset value of the leaf may be determined based on a movement phase of the leaf. In some embodiments, a current movement phase of the leaf may be determined based on measurement values of the main encoder (e.g., a motor encoder) of the driving component and/or the auxiliary encoder (e.g., a Hall sensor) associated with the leaf. The current movement phase of the leaf may be also referred to as a first movement phase. The offset value of the leaf may be determined based on the current movement phase of the leaf. For example, the current position of the leaf as described in 702 may be denoted by a first main encoder value acquired by the main encoder. A phase transition position of the leaf at where the leaf moves from a prior movement phase to the current movement phase may be denoted by a second main encoder value acquired by the main encoder. The offset value of the leaf may be determined based on a difference between the first main encoder value and the second main encoder value and a reference offset value associated with the phase transition position of the leaf. In some embodiments, the offset value of the leaf may be determined based on the current angle of the leaf and the current movement phase of the leaf. More descriptions for determining the offset value of the leaf based on the movement phase of the leaf may be found in FIGS. 9-11 and the descriptions thereof.

In 708, a target position of the leaf may be determined based on the offset value. Operation 708 may be performed by the position adjustment unit 608. As used herein, the target position may be denoted by a main encoder value of the main encoder of the driving component associated with leaf. In some embodiments, the target position may refer to a position determined by calibrating, based on the offset value, the preprogrammed position of the leaf as described in 702. For example, the position adjustment unit 608 may adjust the preprogrammed position of the leaf based on the offset value associated with the current position of the leaf to obtain the target position of the leaf. Further, the target position of the leaf may be determined by subtracting the offset value from the preprogrammed position of the leaf. For example, the leaf is at the current position of 10 millimeters from the reference point (e.g., the front end A of the MLC 200 as shown in FIG. 2A) and in a forward movement direction, and the preprogrammed position of the leaf is 50 millimeter from the reference point. If the offset value of the leaf associated with the current position of 10 millimeters from the reference point determined in 706 is −2 millimeter, then the target position of the leaf may be a difference of the preprogrammed position and the offset value, which is equal to 52 millimeters. The motor may rotate in the second rotation direction to cause the leaf to move in the forward movement direction to the position of 50 millimeters from the reference point. As another example, the leaf is at the current position of 50 millimeters from the reference point and in a backward movement direction, and the preprogrammed position of the leaf is 20 millimeter from the reference point. If the offset value of the leaf associated with the current position of 50 millimeters from the reference point determined in 706 is 1.5 millimeter, then the target position of the leaf may be a difference between the preprogrammed position and the offset value, which is equal to 18.5 millimeters. The motor may rotate in the first rotation direction to cause the leaf to move in the backward movement direction to the position of 20 millimeters from the reference point.

In some embodiments, an actual position (i.e., the target position) of the leaf corresponding to the current position of the leaf may be determined based on the offset value of the leaf. The target position corresponding to the current position may refer to a position determined by calibrating the current position based on the offset value. For example, the position adjustment unit 608 may adjust the current position of the leaf based on the offset value to obtain the target position (i.e., the actual position) of the leaf. Further, the target position (i.e., the actual position) of the leaf corresponding to the current position may be determined by summing the offset value and the current position of the leaf acquired by the main encoder. For example, the leaf is at the current position of 10 millimeters from the reference point (e.g., the front end A of the MLC 200 as shown in FIG. 2A) and in the forward movement direction. If the offset value of the leaf associated with the current position of 10 millimeters determined in 706 is −2 millimeter, then the target position (i.e., the actual position) of the leaf may be a sum of the current position and the offset value, which is equal to 8 millimeters. As another example, the leaf is at the current position of 50 millimeters from the reference point in the backward movement direction. If the offset value of the leaf associated with the current position of 50 millimeters determined in 706 is 1.5 millimeter, then the target position (i.e., the actual position) of the leaf may be a sum between the current position and the offset value, which is equal to 51.5 millimeters.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. For example, operation 706 may be divided into at least two operations. Operations 702 and 704 may be performed simultaneously. Further, a current position of a leaf may be determined. The current position of the leaf may be denoted by the movement direction of the leaf and the angle of the leaf.

FIG. 8 is a flowchart illustrating an exemplary process 800 for determining an offset value of a leaf based on the angle of the leaf and a movement direction of the leaf according to some embodiments of the present disclosure. In some embodiments, one or more operations of process 800 illustrated in FIG. 8 may be implemented in the radiotherapy system 100 illustrated in FIG. 1. For example, process 800 illustrated in FIG. 8 may be stored in the storage device 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operation 706 may be performed according to process 800.

In 802, a first reference offset value of a leaf associated with a current position of the leaf may be obtained based on a movement direction and an angle of the leaf. Operation 802 may be performed by the acquisition module 502. The movement direction of the motor and the angle of the leaf may be determined as described in connection with operations 702 and 704 in FIG. 7.

In some embodiments, the first reference offset value of the leaf may be determined from an offset table (e.g., Offset Table 1 as shown below) associated with an MLC including the leaf based on the movement direction of the leaf and the angle of the leaf. The offset table (e.g., Offset Table 1 as shown below) may include a plurality of reference offset values. Each of the plurality of reference offset values may correspond to one of a plurality of leaves in the MLC (e.g., the MLC 114 as shown in FIG. 1) under a specific angle and a specific movement direction. In some embodiments, the offset table of the MLC may be determined by and/or stored in the radiotherapy system 100. The acquisition module 502 may obtain the reference offset value of the leaf and/or the offset table of the MLC from the storage device 130, the storage 320, the storage 490, the storage module 508, the storage unit 610, and/or any other external storage.

In some embodiments, one of the plurality of reference offset values in the offset table associated with one of the plurality of leaves in the MLC may be determined using a distance measurement device and a main encoder of a driving component (e.g., a motor) when the one of the plurality of leaves is moving in a specific movement direction (e.g., the forward movement direction or the backward movement direction) under a specific angle (e.g., 0 degrees, 45 degrees, 90 degrees, etc.). The main encoder of the driving component (e.g., a motor) associated with the one of the plurality of leaves may be configured to acquire the position of the one of the plurality of leaves that may be inaccurate caused by a position error (e.g., the backlash error) as described elsewhere in the present disclosure. The distance measurement device may be configured to acquire an exact position of one or more of the plurality of leaves. The position (i.e., inaccurate position) of a leaf acquired by the main encoder of the driving component of the leaf may be inaccurate with respect to the position (i.e., exact position) of the leaf acquired by the distance measurement device. Further, the one of the plurality of reference offset values of the one of the plurality of leaves may be determined based on a difference between the exact position and the inaccurate position of the one of the plurality of leaves.

As shown in Offset Table 1, an MLC may include 120 leaves. Each of the plurality of leaves may have a specific leaf ID. Each of the plurality of leaves in the MLC may correspond to different reference offset values under different angles and different movement directions (e.g., the forward movement direction or backward movement direction shown in Offset Table 1). The angle of each of the plurality of leaves may be in a range from −90 degrees to 90 degrees. As used herein, the angle of a leaf is 0 degree if the leaf and a driving component (e.g., a motor) associated with the leaf are both parallel to the horizontal plane. The angle of a leaf is less than 0 degree if the leaf is located above a driving component (e.g., a motor) associated with the leaf. The angle of a leaf is greater than 0 degrees if the leaf is located below a driving component (e.g., a motor) associated with the leaf. In some embodiments, reference offset values of a specific leaf may be measured under a series of coherent angle values (e.g., every 10 degrees) between −90 degrees to 90 degrees. In some embodiments, reference offset values of a specific leaf may be measured under a series of distributed and random angle values (e.g., 10 degrees, 5 degrees, 2 degrees, etc.). As shown in Offset Table 1, the offset value is measured every 10 degrees of the leaf angle. And with a specific degree of the leaf, reference offset values of the specific leaf is measured in two different movement directions, the forward movement direction (i.e. Forward in Offset Table 1) and the backward movement direction (i.e. Backward in Offset Table 1).

OFFSET TABLE 1

| | | Leaf ID | | | | |
|---|---|---|---|---|---|---|
| Leaf angle | Leaf ID | 1 | . . . | 60 | . . . | 120 |
| 90 | Forward | | | | | |
| | Backward | | | | | |
| 80 | Forward | | | | | |
| | Backward | | | | | |
| . . . | | | | | | |
| 0 | Forward | | | | | |
| | Backward | | | | | |
| . . . | | | | | | |
| −80 | Forward | | | | | |
| | Backward | | | | | |
| −90 | Forward | | | | | |
| | Backward | | | | | |

In some embodiments, a relationship between the reference offset value and the current position of a specific leaf in the MLC may be further determined when the leaf with a specific angle is moving at a specific direction. For example, when the leaf with the specific angle is moving at the specific movement direction, multiple positions of the specific leaf may be acquired using the distance measurement device and the main encoder of a driving component (e.g., a motor) respectively. Each of the multiple positions may be denoted by a main encoder value acquired by the main encoder and a measurement value acquired by the distance measurement device. Each of multiple reference offset values associated with the each of the multiple positions of the specific leaf may be determined based on a difference between the main encoder value acquired by the main encoder and the measurement value acquired by the distance measurement device. The relationship between the reference offset value and the position of the specific leaf when the leaf with the specific angle is moving at the specific direction may be determined based on the multiple reference offset values and the multiple positions using, for example, a polynomial fitting technique (e.g., a binomial fitting algorithm). Then, the reference offset value of the leaf associated with the current position may be determined based on the current position and the relationship between the reference offset value and the position of the leaf corresponding to the movement direction and the angle. In some embodiments, the offset table may include multiple relationships between the reference offset value and the position of each of the plurality of leaves under different angles and movement directions. In some embodiments, the offset table may include multiple reference offset values of each of the plurality of leaves under different angles, different movement directions, and different positions. A current reference offset value of a leaf corresponding to the current position may be obtained from the offset table based on the current position of the leaf, the angle of the leaf and the movement direction of the leaf.

In 804, a first main encoder value acquired by a main encoder of a driving component associated with leaf may be obtained, which may be associated with the current position of the leaf. The operation 804 may be performed by the acquisition module 502. The first main encoder value may represent the current position of the leaf. In some embodiments, the first main encoder value may be obtained from the MLC 114, the storage device 130, the storage module 508, the storage unit 610, or any other external storage.

Figure 11:
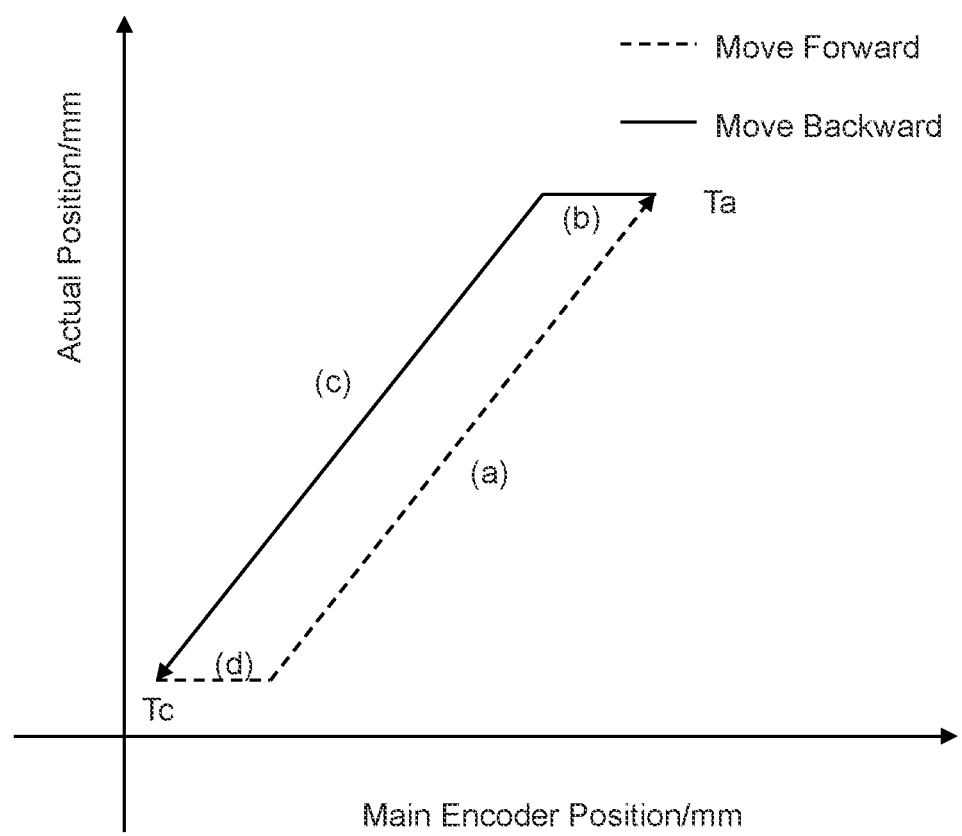
FIG. 11 is a schematic diagram illustrating an exemplary movement curve of a leaf according to some embodiments of the present disclosure.

In 806, a second main encoder value acquired by the main encoder of the driving component associated with the leaf may be obtained, which may be associated with a prior position of the leaf when a movement direction of the leaf (or a rotation direction of the motor) changes. Operation 806 may be performed by the acquisition module 502. The second main encoder value may represent the prior position of the leaf. As used herein, the prior position of the leaf may be also referred to as a direction transition position of the leaf. In some embodiments, when the leaf is at the current position, the movement direction of the leaf may be a first direction including one of the forward movement direction or the backward movement direction as described elsewhere in the present disclosure (e.g., FIG. 6 and the descriptions thereof). When the leaf was at the prior position, the movement direction of the leaf may change from a second direction (e.g., the forward movement direction or the backward movement direction as described elsewhere in the present disclosure (e.g., FIG. 6 and the descriptions thereof)) to the first direction. For example, as shown in FIG. 11, if the leaf is moving in the forward movement direction, the current position of the leaf may correspond to a point on section (a) or section (d) of the movement curve in FIG. 11. The prior position of the leaf may correspond to the transition point Tc. If the leaf is moving in the backward movement direction, the current position of the leaf may correspond to a point on section (b) or section (c) of the movement curve in FIG. 11. The prior position of the leaf may correspond to the transition point Ta. In some embodiments, the second main encoder value may be obtained from a component (e.g., the position feedback module 218) of the control system, the storage device 130, the storage module 508, the storage unit 610, or any other external storage.

In 808, a determination may be made as to whether the movement direction of the leaf moves in the backward movement direction. Operation 808 may be performed by the offset determination unit 606. If it is determined that the movement direction of the leaf corresponding to the current position is the backward movement direction as described elsewhere in the present disclosure, process 800 may proceed to operation 810. If it is determined that the movement direction of the leaf corresponding to the current position is the forward movement direction as described elsewhere in the present disclosure, process 800 may proceed to operation 812.

In 810, a minimum value among the first reference offset value and the sum of a second reference offset value and the difference between the first main encoder value and the second main encoder value may be designated as an offset value of the leaf associated with the current position. Operation 810 may be performed by the offset determination unit 606. The second reference offset value may correspond to the prior position. In some embodiments, when the movement direction of the leaf is the backward movement direction at the current position, the offset value of the leaf may be determined according to Equation (2) below:

$$\text{Offset } Px = \min((\text{Encoder } Ta - \text{Encoder } Px + \text{Offset } Ta), \text{Reference offset } Px), \quad (2),$$

where, Encoder Ta represents a main encoder value (e.g., the second main encoder value) associated with a prior position of a leaf acquired by a main encoder of a driving component when the movement direction of the leaf changes from the forward movement direction to the backward movement direction, Encoder Px represents a main encoder value (e.g., the first main encoder value) associated with a current position of the leaf acquired by the main encoder of the driving component, Offset Ta denotes the second reference offset value associated with the prior position (e.g., transition point Ta as shown in FIG. 11) of the leaf, and Reference offset Px represents a first reference offset value obtained from an offset table when the leaf is moving with the backward movement direction.

In 812, a maximum value among the first reference offset value and the sum of the second reference offset value and the difference between the first main encoder value and the second main encoder value may be designated as an offset value of the leaf associated with the current position. Operation 812 may be performed by the offset determination unit 606. In some embodiments, when the movement direction of the leaf is the forward movement direction at the current position, the offset value of the leaf may be determined according to Equation (3) below:

$$\text{Offset } Px = \max((\text{Encoder } Tc - \text{Encoder } Px + \text{Offset } Tc), \text{Reference offset } Px), \quad (3),$$

where Encoder T2 represents a main encoder value (e.g., the second main encoder value) acquired by a main encoder of a driving component associated with a prior position of a leaf when the movement direction of the leaf changes from the backward movement direction to the forward movement direction, Encoder Px represents a main encoder value (e.g., the first main encoder value) associated with a current position of the leaf acquired by the main encoder of the driving component, Offset Tc denotes the second reference offset value associated with the prior position (e.g., transition point Tc as shown in FIG. 11)) of the leaf, and Reference offset Px represents a first reference offset value obtained from an offset table when the leaf is moving with the forward movement direction.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

For example, operations 804 and 806 may be performed simultaneously or in a reverse order than that illustrated in FIG. 8. As another example, process 800 may further include process a first signal associated with the current position of the leaf acquired by the main encoder of the driving component to obtain the first main encoder value. As still another example, process 800 may further include process a second signal associated with the prior position of the leaf acquired by the main encoder of the driving component to obtain the second main encoder value.

FIG. 9 is a flowchart illustrating another exemplary process 900 for determining an offset value of a leaf according to some embodiments of the present disclosure. In some embodiments, one or more operations of process 900 illustrated in FIG. 9 may be implemented in the radiotherapy system 100 illustrated in FIG. 1. For example, the process 900 illustrated in FIG. 9 may be stored in the storage device 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operation 706 may be performed by process 900 as illustrated in FIG. 9.

In 902, a current movement phase of a leaf corresponding to a current position of the leaf may be determined. Operation 902 may be performed by the movement determination unit 602. In some embodiments, the current movement phase of the leaf may be also referred to as a first movement phase when the leaf is at the current position (i.e., a first position). The current movement phase may be one of the four phases including a first phase, a second phase, a third phase, and a fourth phase. The leaf may be determined in the first phase (also referred to as a forward-movement phase) when the leaf is moving toward the center of a radiation field. The leaf may be determined in the second phase (also referred to as a backward consume phase) when the leaf is static relative to a carriage of an MLC including the leaf and configured to move away from the center of the radiation field.

The leaf may be determined in the third phase (also referred to as a backward movement phase) when the leaf is moving away from the radiation field. The leaf may be determined in the fourth phase (also referred to as a forward consume phase) when the leaf is static relative to the carriage of the MLC including the leaf and configured to move toward the center of the radiation field. More descriptions of the four phases may be found elsewhere in the present disclosure (e.g., FIG. 16A, and the descriptions thereof).

In some embodiments, the movement determination unit 602 may determine the current movement phase of the leaf based on measurements of a main encoder (e.g., a motor encoder) of a driving component and/or an auxiliary encoder (e.g., a Hall sensor) associated with the leaf in two adjacent sampling periods (also referred to as adjacent calculation cycles). As used herein, a measurement of each of the main encoder and/or the auxiliary encoder may include a count of signals acquired by each of the main encoder and/or the second encoder which may be used to determine a position of the leaf. Further, the current movement phase of the leaf may be determined based on a count difference of at least one of the main encoder and/or the second encoder in two adjacent sampling periods (also referred to as adjacent calculation cycles). For example, when the leaf is moving in the forward movement phase, if the count difference between two measurements of the main encoder in adjacent sampling periods is less than a first threshold (e.g., −5, or a constant less than −5), the movement determination unit 602 may determine that the movement phase of the leaf changes and the leaf is moving into the backward consume phase. If the count difference between two measurements of the main encoder in adjacent sampling periods is greater than a second threshold (e.g., −5, or a constant less than −5), the movement determination unit 602 may determine that the movement phase of the leaf changes and the leaf is moving into the forward consume phase.

As another example, when the movement phase of the leaf is unknown, if the count difference between the two measurements of the auxiliary encoder in adjacent sampling periods is larger than a third threshold (e.g., 2, or a constant greater than 2), the movement determination unit 602 may determine the current movement phase of the leaf as moving in the forward movement phase. If the count difference between the two measurements of the auxiliary encoder in adjacent sampling periods is less than a fourth threshold (e.g., −2, or a constant less than −2), the movement determination unit 602 may determine the current movement phase of the leaf as the backward movement phase.

As still another example, when the leaf is moving in the backward consume phase, if the count difference between the two measurements of the auxiliary encoder in adjacent sampling periods is larger than the fifth threshold (e.g. 0), the movement determination unit 602 may determine that the current movement phase of the leaf changes and the leaf is moving into the forward movement phase. If the count difference between the two measurements of the auxiliary encoder in adjacent sampling periods is less than the fifth threshold (e.g. 0), the movement determination unit 602 may determine that the current movement phase of the leaf changes and the leaf is moving into the backward movement phase. When the leaf is moving in the forward consume phase, if the count difference between the two measurements of the auxiliary encoder in adjacent sampling periods is larger than the fifth threshold (e.g. 0), the movement determination unit 602 may determine that the current movement phase of the leaf changes and the leaf is moving into the forward movement phase. If the count difference between the two measurements of the auxiliary encoder in adjacent sampling periods is less than the fifth threshold (e.g. 0), the movement determination unit 602 may determine that the current movement phase of the leaf changes and the leaf is moving into the backward movement phase.

In 904, a reference offset value may be determined, which is associated with a prior position of the leaf at where a movement phase of the leaf changes from a prior movement phase to the current movement phase. Operation 904 may be performed by the offset determination unit 606. As used herein, the prior position may be also referred to as a phase transition position or transition point (e.g., transition points T1, T2, T3, and T4 as shown in FIG. 16A) of the leaf. The prior movement phase may be also referred to as a second movement phase. The prior position may correspond to a transition point closest to the current position of the leaf. For example, if the current movement phase of the leaf determined in 902 is the backward consume phase, the prior movement phase of the leaf may be the forward movement phase. Then the prior position may correspond to a second transition point (e.g., transition point T2 as shown in FIG. 16A) from the forward movement phase to the backward consume phase. If the current movement phase of the leaf determined in 902 is the backward movement phase, the prior the movement phase of the leaf may be the backward consume phase. Then the prior position may correspond to a third transition point (e.g., transition point T3 as shown in FIG. 16A) from the backward consume phase to the backward movement phase.

If the current movement phase of the leaf determined in 902 is the forward movement phase, the prior movement phase of the leaf may be the forward consume phase. Then the prior position may correspond to a first transition point (e.g., transition point T1 as shown in FIG. 16A) from the forward consume phase to the forward movement phase. If the current movement phase of the leaf determined in 902 is the forward consume phase, and the prior movement phase of the leaf is the backward movement phase. Then the prior position may correspond to a fourth transition point (e.g., transition point T4 as shown in FIG. 16A) from the backward movement phase to the forward consume phase.

The reference offset value of the leaf associated with the prior position of the leaf may be an offset value when the leaf is moving at the prior position. In some embodiments, if the leaf is in the forward consume phase, the reference offset value of the leaf may be equal to an offset value corresponding to the fourth transition point (e.g., transition point T4 as shown in FIG. 16A) from the backward movement phase to the forward consume phase. If the leaf is in the backward consume phase, the reference offset value of the leaf may be equal to an offset value corresponding to the second transition point (e.g., transition point T2 as shown in FIG. 16A) from the forward movement phase to the backward consume phase.

In 906, a first main encoder value acquired by a main encoder of a driving component associated with the leaf may be obtained, which is associated with the current position of the leaf. Operation 906 may be performed by the offset determination unit 606. In some embodiments, the first main encoder value may represent the current position of the leaf. In some embodiments, the first main encoder value may be obtained from the main encoder (e.g., the encoder 208) directly. In some embodiments, the first main encoder value may be obtained from the storage device 130, the storage module 508, the storage unit 610, or any other external storage.

In 908, a second main encoder value acquired by the main encoder may be obtained, which is associated with the prior position of the leaf. Operation 908 may be performed by the offset determination unit 606. In some embodiments, the second main encoder value acquired by the main encoder may represent the prior position of the leaf. In some embodiments, the second main encoder value may be obtained from the storage device 130, the storage module 508, the storage unit 610, or any other external storage.

In 910, the offset value may be determined based on the reference offset value and a difference between the first main encoder value and the second main encoder value. Operation 910 may be performed by the offset determination unit 606.

Figure 19A:
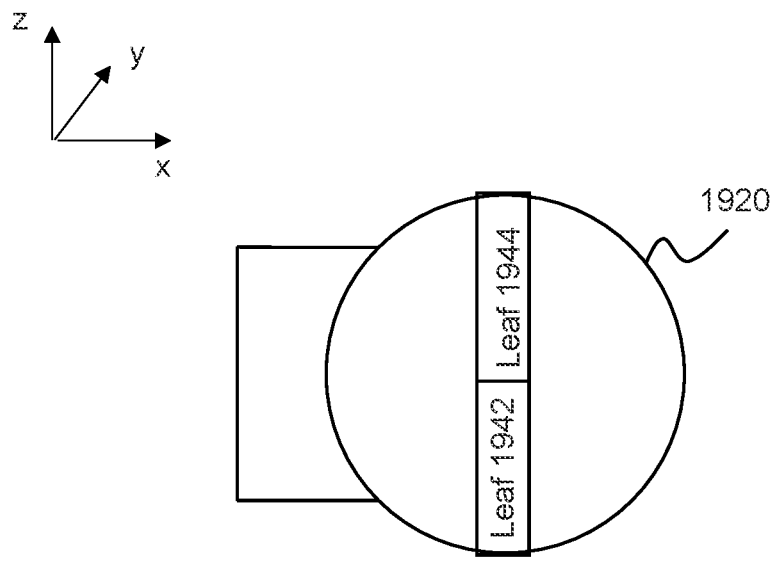
FIG. 19A is a schematic illustrating an exemplary angle relationship between a leaf, collimator, and gantry according to some embodiments of the present disclosure.
Figure 19B:
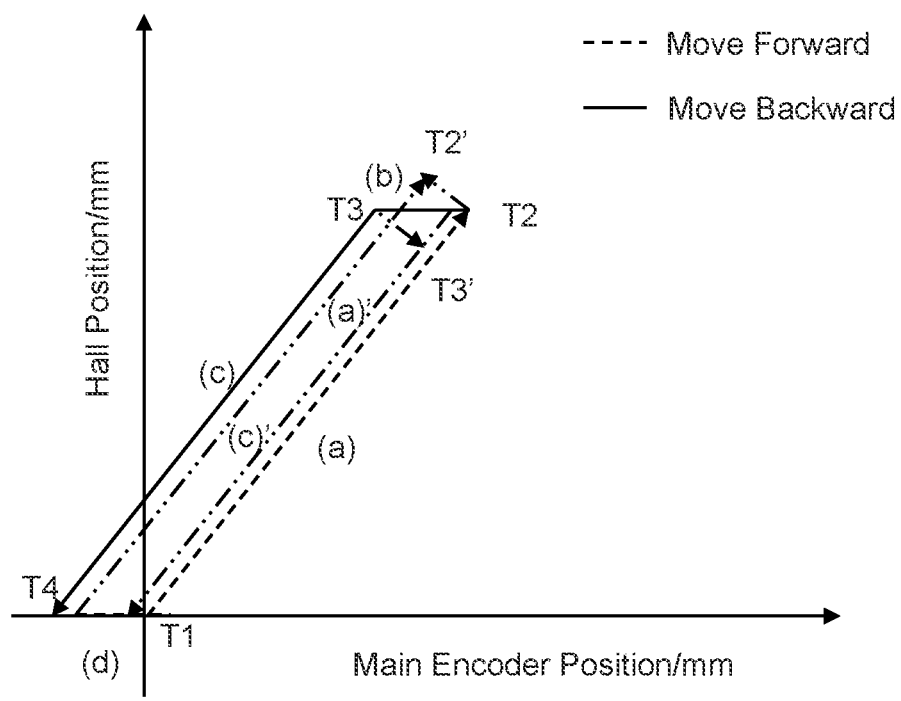
FIG. 19B is a graph illustrating an exemplary movement curve of a leaf according to some embodiments of the present disclosure.

In some embodiments, the offset value of the leaf associated with the current position may be determined based on the reference offset value and the difference between the first main encoder value and the second main encoder value. Further, the offset value of the leaf associated with the current position of the leaf may be equal to a sum between the reference offset value and the difference between the second main encoder value and the first main encoder value as described by Equation (4) below:

$$\text{Offset } Px = \text{Encoder } Tx - \text{Encoder } Px + \text{Reference Offset } Tx, \quad (4),$$

where, Offset Tx represents an offset value corresponding to a current position of a leaf, Encoder Tx represents a main encoder value corresponding to a prior position when a movement phase of the leaf changes from a prior movement phase to a current movement phase, also referred to as the second main encoder value For example, Encoder Tx may correspond to the transition position T2' or T2 as shown in FIG. 19B. Encoder Px represents a main encoder value corresponding to the current position, also referred to as the first main encoder value, and Reference Offset Tx represents a reference offset value corresponding to the prior position. If the current movement phase of the leaf is the backward consume phase, and the prior movement phase is the forward movement phase, the offset value (i.e., Offset Px) of the leaf associated with a current position in the backward consume phase may be determined as described by Equation (5) below:

$$\text{Offset } Px = \text{Encoder } T2 - \text{Encoder } Px + \text{Reference Offset } T2 \quad (5),$$

where Offset Px represents an offset value of the leaf associated with a current position in the backward consume phase, Encoder T2 represents a main encoder value acquired by the main encoder associated with a position when the movement phase of the leaf changes from the forward movement phase to the backward consume phase, i.e., a second main encoder value, and Encoder Px represents a main encoder value acquired by the main encoder associated with the current position in the backward consume phase, i.e., a first main encoder value. Reference Offset T2 represents a reference offset value of the second transition point T2 that may be an offset value of the position when the movement phase of the leaf changes from the forward movement phase to the backward consume phase.

According to Equation (5), if the current position corresponds to the third transition point when the movement phase of the leaf changes from the backward consume phase to the backward movement phase, the offset value of the current position may be denoted by Equation (6):

$$\text{Offset } Px = \text{Offset } T3 = \text{Encoder } T2 - \text{Encoder } T3 + \text{Offset } T2 \quad (6).$$

If the current movement phase of the leaf is the forward consume phase, and the prior movement phase is the backward movement phase, an offset value (i.e., Offset Px) of the leaf associated with the current position in the forward consume phase may be determined as described by Equation (7) below:

$$\text{Offset } Px = \text{Reference Offset } T4 - (\text{Encoder } Px - \text{Encoder } T4) \quad (7).$$

where Offset Px represents an offset value of the leaf associated with the current position in the forward consume phase, Encoder T4 represents a main encoder value (i.e., the second main encoder value) acquired by the main encoder associated with a position when the movement phase of the leaf changes from the backward movement phase to the forward consume phase, Encoder Px represents a main encoder value (i.e., the first main encoder value) acquired by the main encoder associated with the current position in the forward consume phase, and Reference Offset T4 represents a reference offset value of the fourth transition point T4 that may be an offset value of the position when the movement phase of the leaf changes from the backward movement phase to the forward consume phase.

According to Equation (7), if the current position includes the position when the movement phase of the leaf changes from the forward consume phase to the forward movement phase, i.e., the first transition point T1, the offset value of the current position may be denoted by Equation (8):

$$\text{Offset } Px = \text{Offset } T1 = (\text{Encoder } T4 - \text{Encoder } T1 + \text{Offset } T4) \quad (8).$$

In operation 912, the offset value of the current position of the leaf may be determined based on the reference offset value of the prior position. Operation 912 may be performed by the offset determination unit 606. When the leaf is at the prior position, a movement phase of the leaf changes from a prior movement phase to the current movement phase. The prior position may correspond to a transition point closest to the current position of the leaf. More descriptions for the prior position of the leaf may be found in operation 904.

In some embodiments, if the leaf is in the forward movement phase or the backward movement phase, a backlash between the leaf and the driving component may be unchanged, such that the offset value for removing the backlash may be a constant. In other words, the offset value of the leaf may be unchanged when the leaf is moving in the forward movement phase or the backward movement phase.

In some embodiments, if the leaf is in the forward movement phase, the offset value of the current position may be equal to an offset value of a phase transition position (e.g., first transition point T1 as shown in FIG. 16A) from the forward consume phase to the forward movement phase, denoted by offset T1, and may be equal to an offset value of a phase transition position (e.g., second transition point T2 as shown in FIG. 16A) from the forward movement phase to the backward consume direction, denoted by offset T2. In other words, the offset value of the current position in the forward movement phase may be denoted by Offset Px=Offset T1=Offset T2.

In some embodiments, if the leaf is in the backward movement phase, the offset value of the current position may be equal to an offset value of a phase transition position (e.g., third transition point T3 as shown in FIG. 16A) from the backward consume phase to the backward movement phase, denoted by Offset T3, and may be also equal to an offset value of a phase transition position (e.g., fourth transition point T4 as shown in FIG. 16A) from the backward movement phase to the forward consume phase, denoted by offset T4. In other words, the offset value of the current position in the backward movement phase may be denoted by Offset Px=Offset T3=Offset T4.

In some embodiments, if the angle of the leaf is 0 degree and the leaf is in the forward movement phase, the offset value of the leaf may be equal to zero, which may be denoted by Offset Px=Offset T1=Offset T2=0.

In some embodiments, the angle of the leaf may change along with the leaf moves. The change of the angle of the leaf may cause a change of backlash error, and the offset value of the leaf needs to be modified.

If the angle of the leaf is about 0 degree, the angle change of the leaf does not exceed a threshold, and the leaf is in the forward movement phase, the offset value of the current position in the forward movement phase may be equal to 0 that may be denoted by Offset Pr=Offset T1=Offset T2=0. If the leaf is in the backward consume phase, the offset value of the current position in the backward consume phase may be denoted by Offset Px=Encoder T2-Encoder Px. If the leaf is in the backward movement phase, the offset value of the current position in the backward movement phase may denoted by Offset Px=Offset T3=Offset T4=Encoder T2-Encoder T3. If the leaf is in the forward consume phase, the offset value of the current position in the forward consume phase may denoted by Offset Px=(Encoder T2-Encoder T3)-(Encoder Px-Encoder T4).

If the angle change of the leaf exceeds a threshold, the offset value of the current position of the leaf may be determined based on the reference offset value of the prior position.

In some embodiments, if the leaf is in the forward movement phase or the backward movement phase, whether the offset value of the current position needs to be modified may be determined by determining whether the angle change of the leaf exceeds the threshold. In some embodiments, if the leaf is in the forward movement phase or the backward movement phase, whether the offset value of the current position needs to be modified may be determined based on measurements of a main encoder and an auxiliary encoder. More descriptions for determining whether the offset value of the current position needs to be modified may be found in FIG. 10 and the descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, process 900 may include the operation of obtaining the values acquired by the Hall sensor. In some embodiments, operations 906 and 908 may be omitted. The offset value of the leaf associated with the current position may be equal to the reference offset value.

FIG. 10 is a flowchart illustrating an exemplary process 1000 for determining a reference offset value of a leaf according to some embodiments of the present disclosure. In some embodiments, one or more operations of process 1000 illustrated in FIG. 10 may be implemented in the radiotherapy system 100 illustrated in FIG. 1. For example, the process 1000 illustrated in FIG. 10 may be stored in the storage device 130 in the form of instructions, and invoked and/or executed by the processing device 120 (e.g., the processor 310 of the computing device 300 as illustrated in FIG. 3, the GPU 430 or CPU 440 of the mobile device 400 as illustrated in FIG. 4). Operation 904 may be performed according to process 1000 as illustrated in FIG. 10. According to process 1000, the offset value of a leaf may be influenced by the angle change of the leaf moving in the forward movement phase or backward movement phase. However, in the forward consume phase or backward consume phase, the effect of the angle change of the leaf on the offset value of a leaf may be neglected.

In 1002, a determination may be made to as whether an angle change of a leaf exceeds a threshold in a current movement phase. Operation 1002 may be performed by the offset determination unit 606. If it is determined that the angle change of the leaf exceeds the threshold in the current movement phase, process 1000 may proceed to operation 1004. If it is determined that the angle change of the leaf does not exceed the threshold in the current movement phase, process 1000 may proceed to operation 1010.

For example, as shown in FIG. 19S, if the angle change of the leaf does not exceed a threshold in the forward movement phase, the offset value of the leaf at the current position may be equal to the offset value of the transition point T1 i.e., Offset T1. If the angle change of the leaf exceeds the threshold in the forward movement phase, a moving curve of the leaf in the forward movement phase may change from section (a) to section (a)', and the offset value of the leaf at the current position needs to be modified.

As another example, as shown in FIG. 19B, if the angle change of the leaf does not exceed a threshold in the backward movement phase, the offset value of the leaf at the current position may be equal to the offset value of the transition point T3 i.e., Offset T3. If the angle change of the leaf exceeds the threshold in the backward movement phase, a moving curve of the leaf in the backward movement phase may change from section (c) to section (c)', and the offset value of the leaf at the current position needs to be modified.

In some embodiments, whether the angle change of the leaf exceeds the threshold may be determined by determining whether an angle change value of the leaf between a reference position and the current position exceeds a threshold. Further, if the angle change value of the leaf exceeds the threshold, the offset value of the leaf at the current position may be modified. For example, the angle change of the leaf may be determined based on an angle change value of the leaf between the prior position and the current position. In some embodiments, whether the angle change of the leaf exceeds the threshold may be determined by determining whether an angle change value of the leaf at the current position with respect to a prior sampling period exceeds the threshold.

In some embodiments, the angle of the leaf may be determined according to Equation (1) as described in FIG. 7. When the leaf is at the reference position Tr, the angle of the leaf may be $\alpha_{Tr}$. When the leaf is at the current position Px, the angle of the leaf may be $\alpha_{Px}$. The angle change value of the leaf may be denoted by $\Delta\alpha=\alpha_{Px}-\alpha_{Tr}$. Whether the angle change value Aa exceeds the threshold may be determined and the offset value of the leaf may be determined according to the determination that the angle change value Da exceeds the threshold.

In some embodiments, whether the angle change of the leaf exceeds the threshold may be determined based on measurements of a main encoder of a driving component and an auxiliary encoder associated with the current position of the leaf and measurements of a main encoder of a driving component and an auxiliary encoder associated with the reference position of the leaf. For example, if the main encoder includes a motor encoder and the auxiliary encoder includes a Hall sensor, whether the angle change of the leaf exceeds the threshold may be determined based on a change of a measurement Encoder Px of the motor encoder (or the main encoder) associated with the current position Px with respect to a measurement of the motor encoder (or the main encoder) associated with the reference position Tr and a change of a measurement Hall Px of the Hall sensor (or the auxiliary encoder) associated with the current position Px with respect to a measurement of the Hall sensor (or the auxiliary encoder) associated with the reference position Tr. The reference position may include a phase transition position, a position in a prior sampling period, a position between the phase transition position and the position in a prior sampling period, etc.

For example, a first main encoder value and a first auxiliary encoder value of the current position of the leaf may be obtained. The first main encoder value may be acquired by the main encoder when the leaf is at the current position and the first auxiliary encoder value may be acquired by the auxiliary encoder when the leaf is at the current position. A second main encoder value and a second auxiliary encoder value of the phase transition position of the leaf may be obtained. The second main encoder value may be acquired by the main encoder when the leaf is at the phase transition position and the second auxiliary encoder value may be acquired by the auxiliary encoder when the leaf is at the phase transition position. A first difference between the first main encoder value and the second main encoder value. A second difference between the first auxiliary encoder value and the second auxiliary encoder value. Whether the offset value of the leaf needs to be modified may be determined based on the first difference and the second difference.

For example, whether the offset value of the leaf needs to be modified may be determined based on a difference between the first difference and the second difference or a ratio of the first difference and the second difference. If the difference between the first difference and the second difference or the ratio of the first difference and the second difference exceeds a threshold, the angle change of the leaf exceeds the corresponding threshold and the offset value of the leaf needs to be modified may be determined. If the difference between the first difference and the second difference or the ratio of the first difference and the second difference does not exceed the threshold, the angle change of the leaf does not exceed the corresponding threshold and the offset value of the leaf does not need to be modified may be determined.

In 1004, an offset value associated with a reference position in the current movement phase may be determined. Operation 1004 may be performed by the offset determination unit 606. The reference position may be a specific position in the current movement phase. For example, the reference position may be a phase transition position from a prior movement phase to the current movement phase. As another example, the reference position may be a position in a prior sampling period. As still another example, the reference position may be a position between the phase transition position and the position in the prior sampling period.

If the leaf is in the forward movement phase, the offset value of the reference position may be equal to Offset T1. If the leaf is in the backward movement phase, the offset value of the reference position may be equal to Offset T3.

In 1006, measurement values of the main encoder and the auxiliary encoder may be obtained when the leaf is at the current position and the reference position respectively. Operation 1006 may be performed by the offset determination unit 606.

In some embodiments, the main encoder may be a motor encoder. The auxiliary encoder may be a Hall sensor. A first motor encoder value Encoder Px and a first Hall value Hall Px corresponding to the current position Px may be obtained. The first motor encoder value Encoder Px may be acquired by the motor encoder and the first Hall value Hall Px may be acquired by the Hall sensor. A second motor encoder value Encoder Tr and a second Hall value Hall Tr corresponding to the reference position Tr may be obtained. The second motor encoder value Encoder Tr may be acquired by the motor encoder and the second Hall value Hall Tr may be acquired by the Hall sensor. In some embodiments, the first motor encoder value Encoder Px, the first Hall value Hall Px, the second motor encoder value Encoder Tr, and the second Hall value Hall Tr may be obtained from the storage device 130, the storage module 508, the storage unit 610 or any other storage device.

In 1008, the offset value associated with the current position of the leaf may be determined based on the offset value of the reference position and the measurement values of the main encoder and the auxiliary encoder corresponding to the current position and the reference position respectively. Operation 1008 may be performed by the offset determination unit 606. As used herein, the second first ideal reference offset value associated with the prior position may also refer to as a reference offset value associated with the prior position not including the error caused by the Hall sensor.

For example, the main encoder may be a motor encoder. The auxiliary encoder may be a Hall sensor. When the leaf is at the reference position, the offset value of the leaf at the reference position may be determined based on measurement values of the motor encoder and the Hall sensor according to Equation (9):

$$\text{Offset } Tr = (\text{Hall } Tr - \delta) - \text{Encoder } Tr \quad (9),$$

where Offset Tr refers to an offset value of the leaf at the reference position Tr, Hall Tr refers to a measurement value of the Hall sensor when the leaf is at the reference position, i.e., the second Hall value, Encoder Tr refers to a measurement value of the motor encoder when the leaf is at the reference position, i.e., the second motor encoder value, and S refers to a feedback error of the Hall sensor caused by poor linearity and repeatability of the Hall sensor.

When the leaf is at the current position, the offset value of the leaf at the current position may be determined based on measurement values of the motor encoder and the Hall sensor according to Equation (10):

$$\text{Offset } Px = (\text{Hall } Px - \delta) - \text{Encoder } Px \quad (10),$$

where Offset Px refers to an offset value of the leaf at the current position Px, Hall Px refers to a measurement value of the Hall sensor when the leaf is at the current position, i.e., the first Hall value, Encoder Px refers to a measurement value of the motor encoder when the leaf is at the current position, i.e., the first motor encoder value, and S refers to the feedback error of the Hall sensor caused by poor linearity and repeatability of the Hall sensor.

According to Equations (9) and (10), the offset value of the leaf at the current position may be determined according to Equation (11):

$$\text{Offset } Px = \text{Offset } Tr + (\text{Hall } Px - \text{Hall } Tr) - (\text{Encoder } Px - \text{Encoder } Tr) \quad (11).$$

If the leaf is in the forward movement phase, the offset value of the reference position Offset Tr may be equal to Offset T1. If the leaf is in the backward movement phase, the offset value of the reference position Offset Tr may be equal to Offset T3.

According to Equation (11), the feedback error of the Hall sensor may be removed.

In 1010, an offset value of the leaf at a prior position may be determined as the offset value of the leaf at the current position. Operation 1010 may be performed by the offset determination unit 606. More descriptions for determining the offset value of the leaf at the prior position may be found in FIG. 9 and the descriptions thereof.

FIG. 11 is a schematic diagram illustrating an exemplary movement curve of a leaf according to some embodiments of the present disclosure. The movement curve of the leaf may be obtained when the leaf has an angle of 0 degrees as shown in FIG. 14C, also referred to that the leaf is parallel to the horizontal plane. As illustrated in FIG. 11, the horizontal axis (i.e., X-axis) represents a position of the leaf acquired by a main encoder associated with the leaf. The vertical axis (i.e., Y-axis) represents the accurate position of the leaf acquired by a distance measurement device, for example, a laser sensor. The solid line denotes that the leaf is moving along the backward movement direction, i.e., moving away from the center of a radiation field. The dotted line denotes that the leaf is moving along the forward movement direction, i.e., moving toward the center of the radiation field. Thus, two transition points associated with the movement direction of the leaf are shown in FIG. 11. Ta represents the transition point from the forward movement direction to the backward movement direction. Tc represents the transition point from the backward movement direction to the forward movement direction. The movement curve of the leaf includes four sections corresponding to four movement phases of the leaf respectively. Section (a) corresponds to a first phase (also referred to as the forward movement phase) of the leaf that the leaf is moving toward the center of the radiation field. Section (b) corresponds to a second phase (also referred to as backward consume phase) that the leaf is static relative to a carriage of an MLC and configured to move away from the center of the radiation field. Section (c) corresponds to a third phase (also referred to as the backward movement phase) that the leaf is moving away from the center of a radiation field. And section (d) corresponds to a fourth phase (also referred to as forward consume phase) that the leaf is static relative to the carriage of the MLC and configured to move toward the center of the radiation field.

Figure 12:
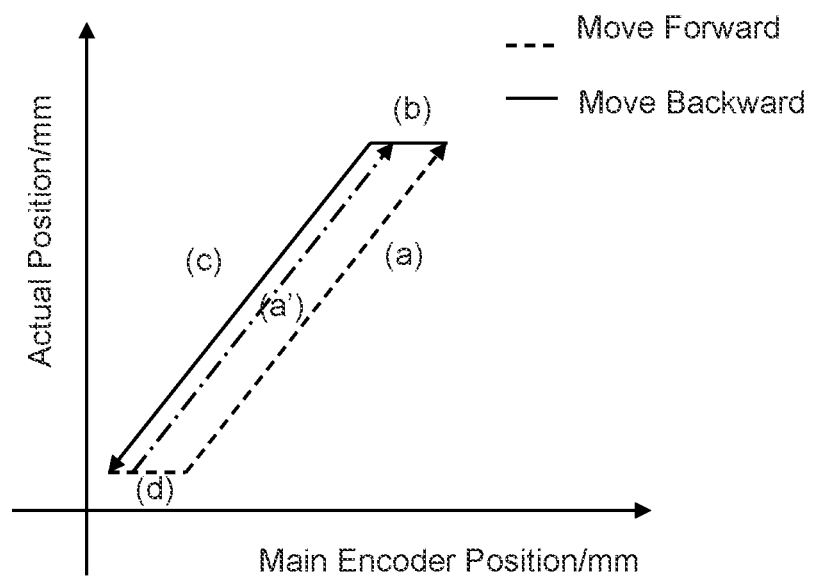
FIG. 12 is a schematic diagram illustrating an exemplary movement curve of a leaf according to some embodiments of the present disclosure.

FIG. 12 is a schematic diagram illustrating an exemplary movement curve of a leaf according to some embodiments of the present disclosure. The movement curve of the leaf is obtained when the leaf is located upward a motor associated with the leaf (e.g., the leaf 1442 with an angle of 90 degrees as shown in FIG. 14B). As shown in FIG. 12, section (a) of the movement curve in FIG. 11 shifts to section (a') causing the shortening of section (b) and section (d), as well as the shifting of the transition point from Ta to Ta'.

Figure 13:
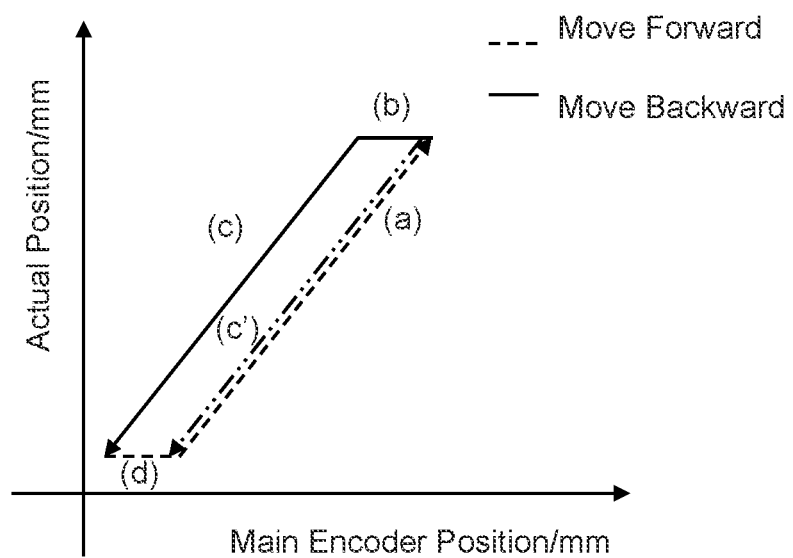
FIG. 13 is a schematic diagram illustrating another exemplary movement curve of a leaf according to some embodiments of the present disclosure.

FIG. 13 is a schematic diagram illustrating another exemplary movement curve of a leaf according to some embodiments of the present disclosure. The movement curve of the leaf is obtained when the leaf is located downward a motor associated with the leaf (e.g., the leaf 1444 with an angle of −90 degrees as shown in FIG. 14B). As shown in FIG. 13, section (c) of the movement curve in FIG. 11 shifts to section (c') causing the shortening of section (b) and section (d), as well as the shifting of the transition point from Tc to Tc'.

FIG. 14A is a schematic diagram illustrating an exemplary gantry of the radiotherapy device 110 in a sectional view according to some embodiments of the present disclosure. In FIG. 14A, a gantry 1420 may include a collimator 1440. An MLC may be mounted on the collimator 1440 and rotate along the collimator 1440. The angle of the gantry (gantry angle) is 90 degrees relative to the horizontal plane as described by a plane formed by X-axis and Y-axis. Z-axis denotes a vertical direction. The direction denoted by arrow "a" corresponds to a direction toward the collimator 1440. Along the direction denoted by the arrow "a", the collimator 1440 may be arranged in different angles relative to the horizontal plane, for example, 90 degrees, 0 degrees, etc.

FIG. 14B and FIG. 14C are schematic diagrams illustrating exemplary leaves of the multi-leaf collimator 1440 in a sectional view according to some embodiments of the present disclosure. As shown in FIG. 14B, the angle of the gantry 1420 is 90 degrees relative to the horizontal plane. The angle of the collimator 1440 is 0 degrees relative to the horizontal plane. Then, the leaf 1442 and the leaf 1444 are vertical to the horizontal plane. The leaf 1442 has an angle of 90 degrees. The leaf 1444 has an angle of −90 degrees. As shown in FIG. 14C, the angle of the collimator 1440 is 90 degrees relative to the horizontal plane, and the leaf 1442 and the leaf 1444 are parallel to the horizontal plane. The angle of the leaf 1442 and the leaf 1444 may be determined based on the angle of the collimator 1440 and the angle of the gantry 1420 according to Equation (1) as described in FIG. 7.

Figure 15:
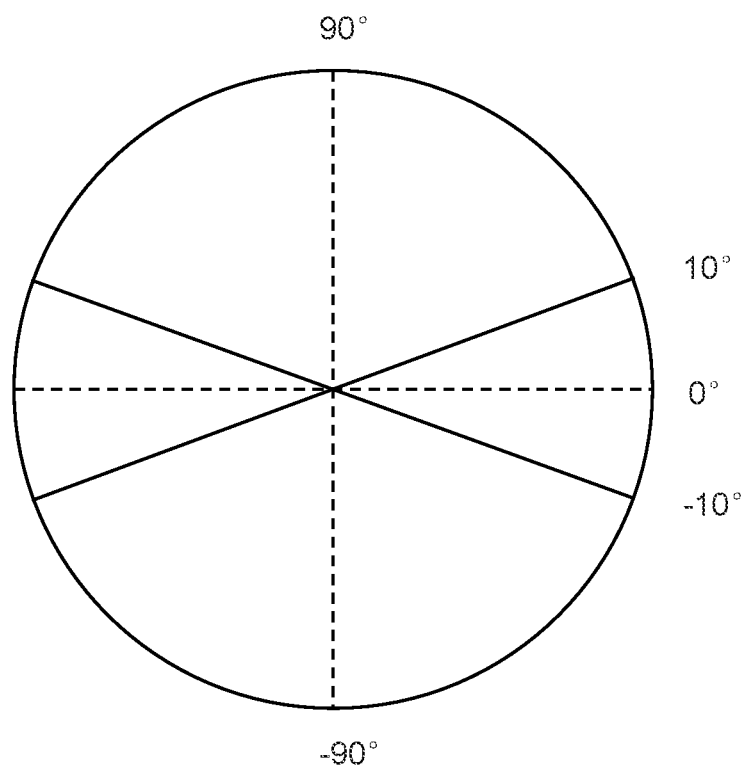
FIG. 15 is a schematic diagram illustrating an exemplary relationship between the angle of a leaf and movement curve of the leaf according to some embodiments of the present disclosure.

FIG. 15 is a schematic diagram illustrating an exemplary relationship between the angle of a leaf and movement curve of the leaf according to some embodiments of the present disclosure. The angle of a leaf (also referred to as leaf angle) may range from −180 degree to 180 degrees. According to large amounts of experiments, the movement curve of the leaf is distributed according to the leaf angle. The movement curves of the leaf with a leaf angle in the range of 0 degrees and 90 degrees are similar to that of the leaf with a leaf angle in the range of 90 degrees to 180 degrees. The movement curves of the leaf with a leaf angle in the range from 0 degrees to −90 degree are similar to that of the leaf with a leaf angle in the range from −90 degree to −180 degree. In a first range between −90 degree and −10 degree, the movement curves of the leaf are similar to the movement curve with the leaf angle of −90 degree, which means the backlash errors of the leaf with a leaf angle in the first range are approximately equal to the backlash error when the leaf angle is −90 degree. In a second range between −10 degree and 10 degree, the movement curves of the leaf are similar to the movement curve with the leaf angle of 0 degree, which means the backlash errors of the leaf with a leaf angle in the second range are approximately equal to the backlash error when the leaf angle is 0 degree. In a third range between 10 degree and 90 degree, the movement curves of the leaf are similar to the movement curve with the leaf angle of 90 degree, which means the backlash errors of the leaf with a leaf angle in the third range are approximately equal to the backlash error when the angle of the leaf is 90 degree.

Figure 16:
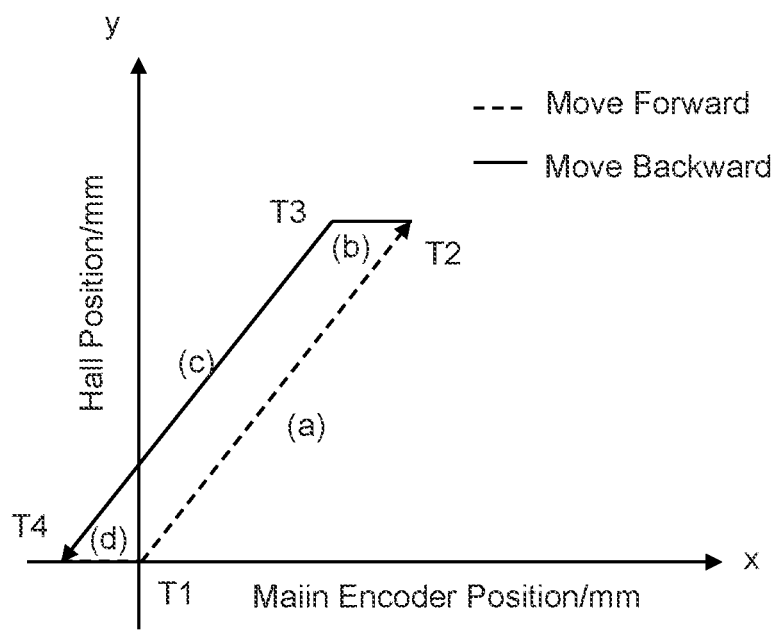
FIG. 16 is a schematic diagram illustrating an exemplary movement curve of a leaf according to some embodiments of the present disclosure.

FIG. 16 is a schematic diagram illustrating an exemplary movement curve of a leaf according to some embodiments of the present disclosure. The movement curve of the leaf may be obtained when the leaf has an angle of 0 degrees. The horizontal axis (i.e., X-axis) shows a position of the leaf which means the position of the leaf being acquired by a main encoder associated with the leaf. The vertical axis (i.e., Y-axis) shows a Hall position of the leaf which means the position of the leaf being acquired by a Hall sensor associated with the leaf. The solid line denotes that the leaf moves away from the center of a radiation field (i.e., the backward movement direction). The dotted line denotes that the leaf moves toward the center of the radiation field (i.e., the forward movement direction). As shown in FIG. 16, the movement curve of the leaf includes four sections corresponding to four movement phases of the leaf respectively. Section (a) corresponds to a first phase (also referred to as the forward movement phase) of the leaf that the leaf is moving toward the center of the radiation field. Section (b) corresponds to a second phase (also referred to as backward consume phase) that the leaf is static relative to a carriage of an MLC and configured to move away from the center of the radiation field. Section (c) corresponds to a third phase (also referred to as the backward movement phase) that the leaf is moving away from the center of the radiation field. And section (d) corresponds to a fourth phase (also referred to as forward consume phase) that the leaf is static relative to the carriage of the MLC and configured to move toward the center of the radiation field. Thus, four transition points associated with four movement phases are shown in FIG. 16. T1 represents a first transition point from the forwarding consume phase to the forward movement phase. T2 represents a second transition point from forward movement phase to the backward consume phase. T3 represents a third transition point from the backward consume phase to the backward movement phase. And T4 represents a fourth transition point from the forward consuming phase to the forward movement phase.

Figure 17:
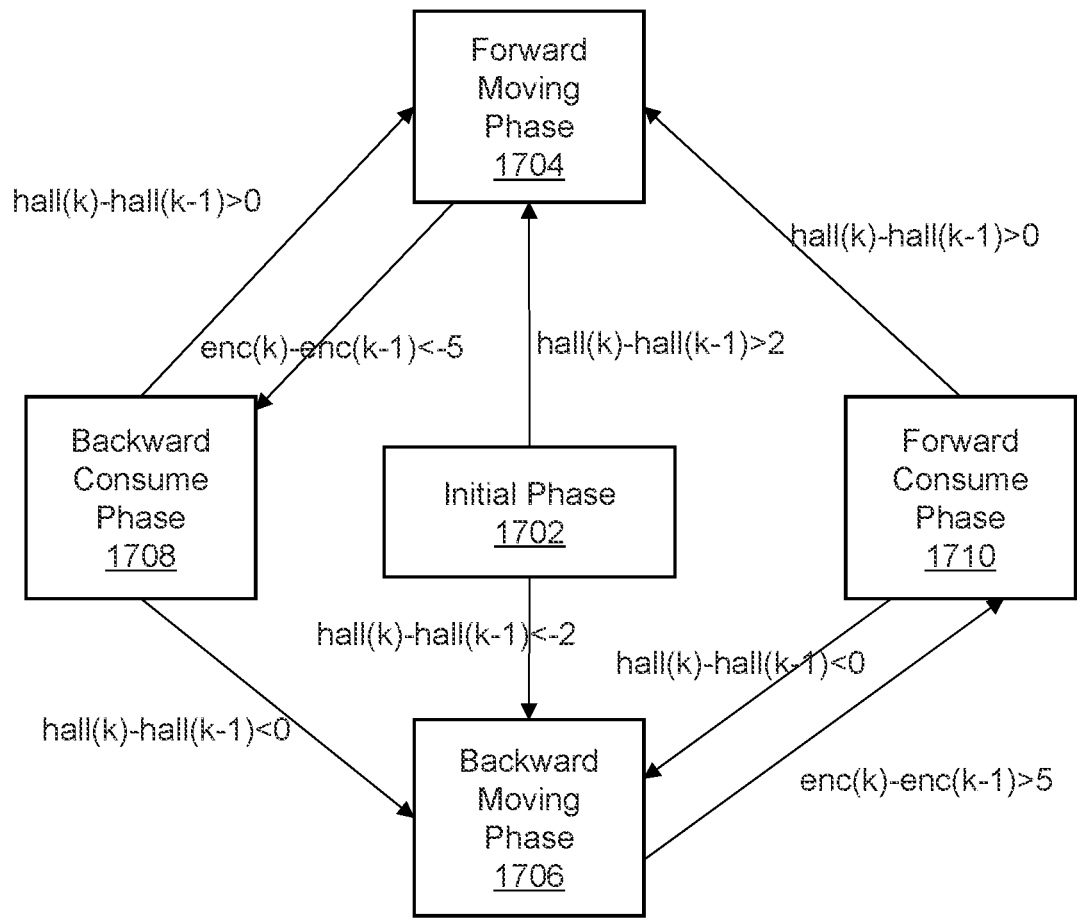
FIG. 17 is a schematic diagram illustrating exemplary movement phases a leaf according to some embodiments of the present disclosure.

FIG. 17 is a schematic diagram illustrating exemplary movement phases a leaf according to some embodiments of the present disclosure. As shown, exemplary movement phases of a leaf may include a forward movement phase 1704, a backward movement phase 1706, a backward consume phase 1708, and a forward consume phase 1710 as described elsewhere in the present disclosure (e.g., FIG. 9 and FIG. 16, and the descriptions thereof). An initial phase of the leaf is unknown corresponding to an initial position of the leaf. The movement phases of the leaf may be determined based on a count difference of a Hall sensor and/or an encoder associated with the leaf between two adjacent calculation cycles, such as kth and (k−1)th. For example, the leaf is determined in the forward movement phase 1704 if a count difference of a Hall sensor associated with the leaf between two adjacent calculation cycles (i.e., Δhall=hall (k)−hall (k−1)) is greater than 2 counts. If the count difference Δhall is less than −2 counts, the leaf is in the backward movement phase 1706. When the leaf is in the forward movement phase 1704, the movement phase of the leaf changes from the forward movement phase 1704 to the backward consume phase 1708 if a count difference of an encoder associated with the leaf between two adjacent calculation cycles (i.e., Δenc=enc(k)−enc(k−1)) is less than −5. When the leaf is in the backward movement phase 1706, the movement phase of the leaf changes from the backward movement phase 1706 to the forward consume phase 1710 if the count difference Δenc is greater than 5 counts.

When the leaf is in the backward consume phase 1708, the movement phase of the leaf changes from the backward consume phase 1708 to the forward movement phase 1704 if the count difference Δhall is greater than 0 counts. On the contrary, the leaf gets into the backward movement phase 1706 with the count difference Δhall less than 0 counts. When the leaf is in the forward consume phase 1710, the movement phase of the leaf changes from the forward consume phase 1710 to the forward movement phase 1704 if the count difference Δhall is greater than 0 counts. On the contrary, the leaf gets into the backward movement phase 1706 with the count difference Δhall less than 0 counts.

Figure 18A:
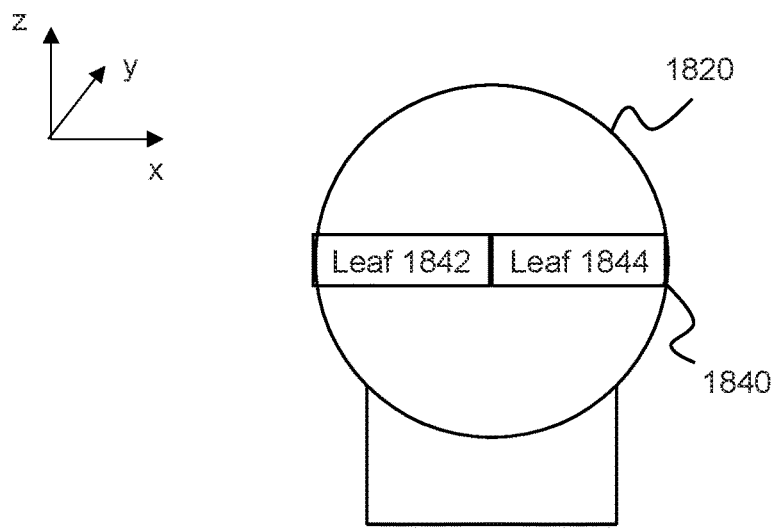
FIG. 18A is a schematic illustrating an exemplary angle relationship between a leaf, collimator, and gantry according to some embodiments of the present disclosure.

FIG. 18A is a schematic illustrating an exemplary angle relationship between a leaf, collimator, and gantry according to some embodiments of the present disclosure. The leaf moves with the rotation of a gantry 1820 and a collimator 1840. As shown in FIG. 18A, an angle of the collimator 1840 is 0 degrees relative to the horizontal plane described by a plane formed by X-axis and Y-axis, which is as same as the angle of the gantry 1820. Z-axis denotes a vertical direction. The angle of the leaf 1842 and the leaf 1844 are determined as 0 degrees relative to the horizontal plane based on the angle of the collimator 1804 and the angle of the gantry 1820 according to Equation (1) as described in FIG. 7.

FIGS. 18B-18E are schematics illustrating exemplary backlash error of a multi-leaf collimator (MLC) according to some embodiments of the present disclosure. A leaf may be driven by a driving component including a ball screw and a motor (not shown). The ball screw may include a screw 1860 and a nut 1880. The screw 1860 and the nut 1880 may be configured with a plurality of teeth (e.g., a screw tooth 1862 on the screw 1860 and a nut tooth 1882 on the nut 1880). The backlash error may exist between the two teeth on the screw 1860 and the nut 1880 respectively when the motor changes rotation direction. FIGS. 18B-18E show backlash errors relating to the driving component of the leaf corresponding to the four movement phases as described elsewhere in the present disclosure (e.g., FIG. 16A).

Figure 18B:
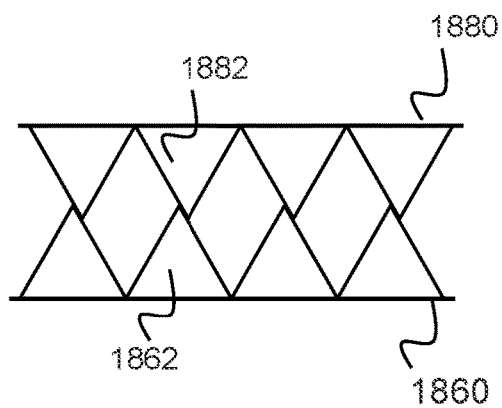
FIG. 18B-18E are schematics illustrating exemplary backlash error of a multi-leaf collimator (MLC) according to some embodiments of the present disclosure.

As shown in FIG. 18B, the leaf is in the forward movement phase driven by the motor associated with the leaf. Two teeth (e.g., the screw tooth 1862 and the nut tooth 1882) on the screw 1860 and the nut 1840 respectively are contacted by each other. There is no backlash between the two teeth (e.g., the screw tooth 1862 and the nut tooth 1882) on the screw 1860 and the nut 1880 respectively.

Figure 18C:
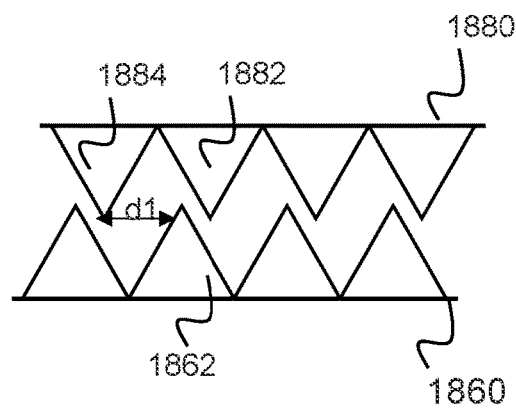

As shown in FIG. 18C, the motor changes the rotation direction and the leaf is in the backward consume phase. There is a backlash error (e.g., distance d1) between two teeth (e.g., the screw tooth 1862 and the nut tooth 1884 adjacent to the nut tooth 1882) on the screw 1860 and the nut 1880 respectively.

Figure 18D:
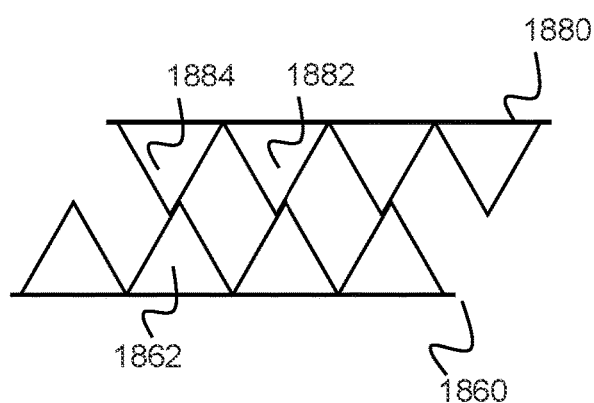

As shown in FIG. 18D, the leaf is in the backward movement phase driven by the motor associated with the leaf. Two teeth (e.g., the screw tooth 1862 and the nut tooth 1884) on the screw 1860 and the nut 1880 respectively are contacted by each other. There is no backlash between the two teeth (e.g., the screw tooth 1862 and the nut tooth 1884 adjacent to the nut tooth 1882) on the screw 1860 and the nut 1880 respectively.

Figure 18E:
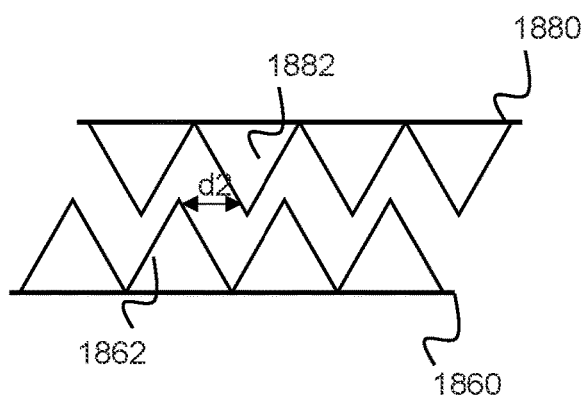

As shown in FIG. 18E, the motor changes the rotation direction and the leaf is in the forward consume phase. There is a backlash error (e.g., distance d2) between two teeth (e.g., the screw tooth 1862 and the nut tooth 1882) on the screw 1860 and the nut 1880 respectively.

FIG. 19A is a schematic illustrating an exemplary angle relationship between a leaf, collimator, and gantry according to some embodiments of the present disclosure. The leaf moves with the rotation of a gantry and a collimator 1920. As shown in FIG. 19A, an angle of the collimator 1920 is 0 degrees relative to the horizontal plane, which is perpendicular to the gantry 1802. The angle of the leaf is determined as 90 degrees relative to the horizontal plane based on the angle of the collimator 1920 and the angle of the gantry according to Equation (1) as described in FIG. 7.

FIG. 19B is a schematic diagram illustrating an exemplary movement curve of a leaf described in FIG. 19A according to some embodiments of the present disclosure. When an angle of the leaf changes from 0 degrees to 90 degrees in the forward movement phase, the movement curve of the leaf corresponding to the forward movement phase moves from section (a) to section (a)'. The second transition point T2 also moves to point T2'. When an angle of the leaf changes from 0 degrees to −90 degrees in the backward movement phase, the movement curve of the leaf corresponding to the backward movement phase moves from section (c) to section (c)'. The third transition point T3 also moves to point T3'.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages.

The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. A method implemented on a computing device having at least one processor and at least one computer-readable storage medium for correcting position errors for a multi-leaf collimator (MLC), the MLC including a plurality of leaves to shape a radiation field, each of the plurality of leaves being associated with a driving component including a main encoder, the method comprising:
    determining a first position for a leaf of the plurality of leaves;
    determining at least one of a first movement direction or a first angle of the leaf at the first position, wherein a movement of the leaf along the first movement direction is configured to move toward or away from a center of the radiation field, and the first angle of the leaf is determined by:
        obtaining an angle of a gantry corresponding to the first position of the leaf;
        obtaining an angle of a collimator corresponding to the first position of the leaf,
    wherein the MLC is mounted in the collimator and rotates along with the collimator; and
        determining the first angle of the leaf based on the angle of the gantry and the angle of the collimator;
    determining an offset value associated with the first position based on at least one of the first angle or the first movement direction; and
    determining a target position of the leaf based on the offset value.

2. The method of claim 1, wherein the first movement direction is determined by:
    obtaining a first velocity relating to the driving component;
    in response to a determination that the first velocity relating to the driving component is lower than a first threshold, determining the first movement direction as a backward movement direction, the leaf being configured to move away from the center of the radiation field along the backward movement direction; and
    in response to a determination that the first velocity relating to the driving component is greater than a second threshold, determining the first movement direction as a forward movement direction, the leaf being configured to move toward the center of the radiation field along the forward movement direction.

3. The method of claim 1, wherein the determining a target position of the leaf based on the offset value includes:
    subtracting the offset value from a preprogrammed position of the leaf.

4. The method of claim 1, wherein the determining an offset value associated with the first position based on at least one of the first angle or the first movement direction includes:
    obtaining a first reference offset value associated with the first position of the leaf from a pre-determined offset table based on at least one of the first angle or the first movement direction;
    obtaining a first main encoder value corresponding to the first position of the leaf, the first main encoder value being acquired by the main encoder;

obtaining a second main encoder value corresponding to a second position of the leaf, the second main encoder value being acquired by the main encoder, and the second position being a position at where a movement direction of the leaf changes from a second movement direction to the first movement direction; and determining the offset value associated with the first position based on the first movement direction, the first reference offset value, and a difference between the first main encoder value and the second main encoder value.

5. The method of claim 4, wherein the determining the offset value associated with the first position based on the first movement direction, the first reference offset value, and a difference between the first main encoder value and the second main encoder value includes:

if the leaf moves away from the center of the radiation field along the first movement direction, designating a minimum value among the first reference offset value and a sum of a second reference offset value associated with the second position and the difference between the first main encoder value and the second main encoder value as the offset value associated with the first position; and if the leaf moves toward the center of the radiation field along the first movement direction, designating a maximum value among the first reference offset value and a sum of the second reference offset value associated with the second position and the difference between the first main encoder value and the second main encoder value as the offset value associated with the first position.

6. The method of claim 1, wherein the determining an offset value associated with the first position based on at least one of the first angle or the first movement direction includes:

if the leaf moves toward the center of the radiation field along the first movement direction and the first angle is equal to 0 degrees, designating the offset value associated with the first position as 0.

7. The method of claim 1, wherein the determining a target position of the leaf based on the offset value includes:

obtaining a first main encoder value corresponding to the first position of the leaf acquired by the main encoder; and correcting the first main encoder value based on the offset value to obtain the target position of the leaf.

8. The method of claim 7, wherein the correcting the first main encoder value based on the offset value includes:

adding the offset value to the first main encoder value to obtain the target position of the leaf.

9. A method implemented on a computing device having at least one processor and at least one computer-readable storage medium for correcting position errors for a multi-leaf collimator (MLC), the MLC including a plurality of leaves to shape a radiation field, each of the plurality of leaves being associated with a driving component including a main encoder, the method comprising:

determining a first position for a leaf of the plurality of leaves;

determining a first movement phase of the leaf at the first position, wherein the leaf in the first movement phase is configured to move toward or away from a center of the radiation field;

determining an offset value associated with the first position based on a determination whether the leaf in the first movement phase moves toward or away from a center of the radiation field; and determining a target position of the leaf based on the offset value;

wherein the first movement phase of the leaf at the first position is determined based on a difference between a first measurement value and a second measurement value acquired by at least one of the main encoder or an auxiliary encoder in two sampling periods.

10. The method of claim 9, wherein the first movement phase includes one of:

a first phase in which the leaf is moving toward the center of the radiation field;

a second phase in which the leaf is static relative to a carriage of the MLC and is directed to move away from the center of the radiation field;

a third phase in which the leaf is moving away from the center of the radiation field; and a fourth phase in which the leaf is static relative to the carriage of the MLC and is directed to move toward the center of the radiation field.

11. The method of claim 10, wherein the determining an offset value associated with the first position based on the first movement phase includes:

in response to a determination that the first movement phase is the second phase or the fourth phase, determining a reference offset value associated with a second position of the leaf, the second position corresponding to a position at where a movement phase of the leaf changes from a second movement phase to the first movement phase;

obtaining a first main encoder value corresponding to the first position of the leaf, the first main encoder value being acquired by the main encoder;

obtaining a second main encoder value corresponding to the second position of the leaf, the second main encoder value being acquired by the main encoder; and determining the offset value associated with the first position based on a difference between the first main encoder value and the second main encoder value and the reference offset value associated with the second position.

12. The method of claim 10, wherein the determining an offset value associated with the first position based on the first movement phase includes:

in response to a determination that the first movement phase is the first phase or the third phase, the offset value associated with the first position is constant.

13. The method of claim 12, wherein the offset value associated with the first position is equal to a reference offset value associated with a second position at where a movement phase of the leaf changes from a second movement phase to the first movement phase.

14. The method of claim 13, further comprising:

determining whether an angle change value of the leaf between angles of the leaf at the first position and the second position exceeds a preprogrammed threshold; and in response to a determination that the angle change value exceeds the preprogrammed threshold, correcting the offset value associated with the first position of the leaf.

15. The method of claim 13, further comprising:

obtaining a first main encoder value and a first auxiliary encoder value corresponding to the first position of the each of the plurality of leaves, the first main encoder value being acquired by the main encoder, the first auxiliary encoder value being acquired by the auxiliary encoder;

obtaining a second main encoder value and a second auxiliary encoder value corresponding to the second position, the second main encoder value being acquired by the main encoder, the second auxiliary encoder value being acquired by the auxiliary encoder;

determining a first difference between the first main encoder value and the second main encoder value;

determining a second difference between the first auxiliary encoder value and the second auxiliary encoder value;

determining whether the offset value associated with the first position needs to be corrected based on the first difference and the second difference; and correcting the offset value associated with the first position of the leaf.

16. The method of claim 14, wherein one of the angles of the leaf is determined by:

obtaining an angle of a gantry corresponding to the first position of the leaf;

obtaining an angle of a collimator corresponding to the first position of the leaf, wherein the MLC is mounted in the collimator and rotates along with the collimator; and determining the angle of the leaf based on the angle of the gantry and the angle of the collimator.

17. The method of claim 10, wherein if the first movement phase is the first phase and an angle of the leaf at the first position is equal to 0 degrees, the offset value associated with the first position is equal to 0.

18. The method of claim 9, wherein the determining a target position of the leaf based on the offset value includes:

subtracting the offset value from a preprogrammed position of the leaf.

19. A system for correcting position errors for a multi-leaf collimator (MLC), the MLC including a plurality of leaves to shape a radiation field, each of the plurality of leaves being associated with a driving component including a main encoder, the system comprising:

at least one storage device storing executable instructions, and at least one processor in communication with the at least one storage device, when executing the executable instructions, causing the system to:

determine a first position for a leaf of the plurality of leaves;

determine at least one of a first movement direction or a first angle of the leaf at the first position, wherein a movement of the leaf along the first movement direction is configured to move toward or away from a center of the radiation field, and the first angle of the leaf is determined by:

obtaining an angle of a gantry corresponding to the first position of the leaf;

obtaining an angle of a collimator corresponding to the first position of the leaf, wherein the MLC is mounted in the collimator and rotates along with the collimator; and determining the first angle of the leaf based on the angle of the gantry and the angle of the collimator;

determine an offset value associated with the first position based on at least one of the first angle or the first movement direction; and determine a target position of the leaf based on the offset value.

20. The method of claim 9, wherein the two sampling periods are two adjacent sampling periods, the first measurement value corresponds to the first position, and the auxiliary encoder is associated with the leaf and configured to determine a position of the leaf.

* * * * *